(12) United States Patent
Kuchroo et al.

(10) Patent No.: US 9,962,440 B2
(45) Date of Patent: *May 8, 2018

(54) METHODS RELATED TO TIM 3, A TH1-SPECIFIC CELL SURFACE MOLECULE, FOR ACTIVATING ANTIGEN PRESENTING CELLS

(71) Applicants: THE BRIGHAM AND WOMEN'S HOSPITAL, INC., Boston, MA (US); DANA-FARBER CANCER INSTITUTE, INC., Boston, MA (US)

(72) Inventors: Vijay K. Kuchroo, Newton Center, MA (US); Sumone Chakravarti, Victoria (AU); Catherine A. Sabatos-Peyton, West Newton, MA (US); Gordon J. Freeman, Brookline, MA (US)

(73) Assignees: The Brigham and Women's Hospital, Inc., Boston, MA (US); Dana-Farber Cancer Institute, Inc., Boston, MA (US)

(*) Notice: Subject to any disclaimer, the term of this patent is extended or adjusted under 35 U.S.C. 154(b) by 650 days.

This patent is subject to a terminal disclaimer.

(21) Appl. No.: 14/464,455

(22) Filed: Aug. 20, 2014

(65) Prior Publication Data
US 2015/0044229 A1 Feb. 12, 2015

Related U.S. Application Data

(63) Continuation of application No. 14/185,050, filed on Feb. 20, 2014, which is a continuation of application No. 13/331,387, filed on Dec. 20, 2011, now Pat. No. 8,697,069, which is a continuation of application No. 12/276,977, filed on Nov. 24, 2008, now Pat. No. 8,101,176, which is a continuation of application No. 10/354,447, filed on Jan. 30, 2003, now Pat. No. 7,470,428.

(60) Provisional application No. 60/353,107, filed on Jan. 30, 2002.

(51) Int. Cl.
*A61K 39/395* (2006.01)
*C07K 16/28* (2006.01)
*C07K 16/18* (2006.01)
*A61K 9/00* (2006.01)
*A61K 45/06* (2006.01)
*A61K 39/00* (2006.01)

(52) U.S. Cl.
CPC ........ *A61K 39/3955* (2013.01); *A61K 9/0019* (2013.01); *A61K 45/06* (2013.01); *C07K 16/18* (2013.01); *C07K 16/28* (2013.01); *A61K 2039/505* (2013.01); *C07K 2317/34* (2013.01); *C07K 2317/50* (2013.01)

(58) Field of Classification Search
None
See application file for complete search history.

(56) References Cited

U.S. PATENT DOCUMENTS

| 6,084,083 A | 7/2000 | Levinson |
| 6,562,343 B1 | 5/2003 | Levinson |
| 6,599,912 B1 | 7/2003 | Au et al. |
| 6,632,608 B2 | 10/2003 | Glimcher et al. |
| 7,470,428 B2 | 12/2008 | Kuchroo et al. |
| 8,697,069 B2 * | 4/2014 | Kuchroo ................ C07K 16/28 424/130.1 |
| 9,333,256 B2 * | 5/2016 | Kuchroo ................ C07K 16/28 |
| 2003/0124114 A1 | 7/2003 | McIntire et al. |
| 2005/0191721 A1 | 9/2005 | Kuchroo et al. |

FOREIGN PATENT DOCUMENTS

| WO | 00/73498 A1 | 12/2000 |
| WO | 03/002722 A3 | 1/2003 |
| WO | 2005/033144 A2 | 4/2005 |

OTHER PUBLICATIONS

Beatty et al. J. Immunology, IFN-gamma Can Promote Tumor Evasion of the Immune System in Vivo by Down-Regulating Cellular Levels of an Endogenous Tumor Antigen, The Journal of Immunology 165:5502-5508 (2000).
Bonnefoy, Cancer Vaccine, Expert Opin. Ther. Targets 8(6):521-525 (2004).
European Patent Office/EP Examination Report for Application No. 03723627.0-2402, dated Jun. 16, 2006.
Genbank Accession No. AAL65156—T cell immunoglobulin mucin-3 [Mus musculus] Feb. 11, 2002.
Genbank Accession No. AAL65157—T cell immunoglobulin mucin-3 [*Homo sapiens*] Feb. 11, 2002.
Genbank Accession No. AAL65158—T cell immunoglobulin mucin-3 [*Homo sapiens*] Feb. 11, 2002.
Genbank Accession No. AF450241—Mus musculus T cell immunoglobulin mucin-3 mRNA, complete cds Feb. 11, 2002.
Genbank Accession No. AF450242—*Homo sapiens* clone 1 T cell immunoglobulin mucin-3 (TIM3) mRNA, complete cds Feb. 11, 2002.
Genbank Accession No. AF450243—*Homo sapiens* clone 2 T cell immunoglobulin mucin-3 (TIM3) mRNA, complete cds Feb. 11, 2002.

(Continued)

*Primary Examiner* — Yunsoo Kim
(74) *Attorney, Agent, or Firm* — Nixon Peabody LLP; Mark J. FitzGerald; Srividya Subramanian

(57) ABSTRACT

The present invention provides compositions and methods useful for promoting or reducing T-cell trafficking to a target tissue. Also provided are compositions and methods useful for promoting or inhibiting antigen-presenting cell (APC) activation. The invention is related to discovery of functional characteristics of TIM-3, a molecule that is preferentially expressed on the surface of Th1 cells. The methods are useful for treating disorders including cancer, infectious disease, allergy, asthma, and autoimmune disease.

17 Claims, 14 Drawing Sheets

(56) References Cited

OTHER PUBLICATIONS

Gordon EJ et al. Both anti-CD11a (LFA-1) and anti-CD11b (MAC-1) therapy delay the onset and diminish the severity of experimental autoimmune encephalomyelitis. J Neuroimmunol 62:153-60 (1995).

Huitinga I et al. Suppression of experimental allergic encephalomyelitis in Lewis rats after elimination of macrophages. J Exp Med 172:1025-1033 (1990).

Kuchroo VJ et al. The TIM gene family: emerging roles in immunity and disease. Nat Rev Immunol. 3(6):454-62 Jun. 2003.

McIntire, J., et al. "Identification of Tapr (an airway hyperreactivity regulatory locus) and the linked Tim gene Family", Nature Immunology, GB, 2(12):1109-1116 (2001).

Monney L et al. Th1-specific cell surface protein Tim-3 regulates macrophage activation and severity of an autoimmune disease. Nature 415:536-541 (2002).

Monney, L., et al. "A Novel Cell Surface Protein, TIM-3, Expressed on TH1 Cells Promotes Macrophage Activation and Enhances Autoimmune Disease", Faseb Journal, Bethesda, US, 16(5): A1062 (2002).

Mosmann TR et al. Two types of murine helper T cell clone. I. Definition according to profiles of lymphokine activities and secreted proteins. J Immunol 136:2348-57 (1986).

Meyers, et al. "The TIM gene family regulates autoimmune an allergic disases", Trends in Molecular Medicine, 11(8): 362-369 (2005).

Nelson et al. Journal of Immunology,166:5557-5566 (2001).

Ngo et al., The Protein Folding Problem and Tertiary Structure Prediction, 492-495 (1994).

Sabatos, C., et. "Interaction of Tim-3 and Tim-3 ligand regulates T helper type 1 responses and induction of peripheral tolerance", Nature Immunology, GB, 4(11):1102-1110 (2003).

Sallusto F et al. Flexible programs of chemokine receptor expression on human polarized T helper 1 and 2 lymphocytes. J Exp Med 187:875-883 (1998).

Syrbe U et al. Th1/Th2 subsets: distinct differences in homing and chemokine receptor expression? Springer Semin Immunopathol 21:263-85 (1999).

Tran EH et al. Immune invasion of the central nervous system parenchyma and experimental allergic encephalomyelitis, but not leukocyte extravasation from blood, are prevented in macrophage-depleted mice. J Immunol 161:3767-3775 (1998).

Venkataraman C et al. Cutting edge: Chandra, a novel four-transmembrane domain protein differentially expressed in helper type 1 lymphocytes. J Immunol 165:632-636 (2000).

Waldner H et al. Fulminant spontaneous autoimmunity of the central nervous system in mice transgenic for the myelin proteolipid protein-specific T cell receptor. Proc Natl Acad Sci USA 97:3412-3417 (2000).

Gordon et al., J. Neuroimmunobiology, 1995, vol. 63, pp. 153-160.

* cited by examiner

SEQUENCE LISTING

```
<160> NUMBER OF SEQ ID NOS: 13

<210> SEQ ID NO 1
<211> LENGTH: 2725
<212> TYPE: DNA
<213> ORGANISM: Mus musculus

<400> SEQUENCE: 1
ttttaaccga ggagctaaag ctatccctac acagagctgt ccttggattt cccctgccaa      60
gtactcatgt tttcaggtct taccctcaac tgtgtcctgc tgctgctgca actactactt     120
gcaaggtcat tggaagatgg ttataaggtt gaggttggta aaaatgccta tctgccctgc     180
agttacactc tacctacatc tgggacactt gtgcctatgt gctgggcaa gggattctgt      240 ccttggtcac agtgtaccaa tgagttgctc agaactgatg aaagaaatgt gacatatcag     300
aaatccagca gataccagct aaagggcgat ctcaacaaag gagatgtgtc tctgatcata     360
aagaatgtga ctctggatga ccatgggacc tactgctgca ggatacagtt ccctggtctt     420
atgaatgata aaaattaga actgaaatta gacatcaaag cagccaaggt cactccagct      480
cagactgccc atgggactc tactacagct tctccaagaa ccctaaccac ggagagaaat     540
ggttcagaga cacagacact ggtgaccctc cataataaca atggaacaaa aatttccaca     600
tgggctgatg aaattaagga ctctggagaa acgatcagaa ctgctatcca cattggagtg     660
ggagtctctg ctgggttgac cctggcactt atcattggtg tcttaatcct taaatggtat     720
tcctgtaaga aaaagaagtt atcgagtttg agccttatta cactggccaa cttgcctcca     780
ggagggttgg caaatgcagg agcagtcagg attcgctctg aggaaaatat ctacaccatc     840
gaggagaacg tatatgaagt ggagaattca aatgagtact actgctacgt caacagccag     900
cagccatcct gaccgcctct ggactgccac ttttaaaggc tcgccttcat ttctgacttt     960
ggtatttccc ttttgaaaa ctatgtgata tgtcacttgg caacctcatt ggaggttctg    1020
accacagcca ctgagaaaag agttccagtt ttctggggat aattaactca caggggatt    1080 cgactgtaac tcatgctaca ttgaaatgct ccattttatc cctgagtttc agggatcgga    1140
tctcccactc cagagacttc aatcatgcgt gttgaagctc actcgtgctt tcatacatta    1200
ggaatggtta gtgtgatgtc tttgagacat agaggtttgt ggtatatccg caaagctcct    1260
gaacaggtag ggggaataaa gggctaagat aggaaggtgc ggttctttgt tgatgttgaa    1320
aatctaaaga agttggtagc ttttctagag atttctgacc ttgaaagatt aagaaaaagc    1380
caggtggcat atgcttaaca cgatataact tgggaacctt aggcaggagg gtgataagtt    1440
caaggtcagc cagggctatg ctggtaagac tgtctcaaaa tccaaagacg aaaataaaca    1500
tagagacagc aggaggctgg agatgaggct cggacagtga ggtgcatttt gtacaagcac    1560
gaggaatcta tatttgatcg tagaccccac atgaaaaagc taggcctggt agagcatgct    1620
tgtagactca agagatggag aggtaaaggc acaacagatc cccggggctt gcgtgcagtc    1680
agcttagcct aggtgctgag ttccaagtcc acaagagtcc ctgtctcaaa gtaagatgga    1740
ctgagtatct ggcgaatgtc catgggggtt gtcctctgct ctcagaagag acatgcacat    1800
gaacctgcac acacacacac acacacacac acacacacac acacacacac acatgaaa     1860
```

```
tgaaggttct ctctgtgcct gctacctctc tataacatgt atctctacag gactctcctc    1920
tgcctctgtt aagacatgag tgggagcatg gcagagcagt ccagtaatta attccagcac    1980
tcagaaggct ggagcagaag cgtggagagt tcaggagcac tgtgcccaac actgccagac    2040
tcttcttaca caagaaaaag gttaccgca agcagcctgc tgtctgtaaa aggaaaccct    2100
gcgaaaggca aactttgact gttgtgtgct caaggggaac tgactcagac aacttctcca    2160
ttcctggagg aaactggagc tgtttctgac agaagaacaa ccggtgactg ggacatacga    2220
aggcagagct cttgcagcaa tctatatagt cagcaaaata ttctttggga ggacagtcgt    2280
caccaaattg atttccaagc cggtggacct cagtttcatc tggcttacag ctgcctgccc    2340
agtgcccttg atctgtgctg ctcccatct ataacagaat caaattaaat agaccccgag    2400
tgaaaatatt aagtgagcag aaaggtagct ttgttcaaag atttttttgc attggggagc    2460
aactgtgtac atcagaggac atctgttagt gaggacacca aaacctgtgg taccgttttt    2520
tcatgtatga attttgttgt ttaggttgct tctagctagc tgtggaggtc ctggcttttct    2580 taggtgggta tggaagggag accatctaac aaaatccatt agagataaca gctctcatgc    2640
agaagggaaa actaatctca aatgttttaa agtaataaaa ctgtactggc aaagtacttt    2700
gagcatattt aaaaaaaaaa aaaaa                                          2725
```

<210> SEQ ID NO 2
<211> LENGTH: 281
<212> TYPE: PRT
<213> ORGANISM: Mus musculus

<400> SEQUENCE: 2

```
Met Phe Ser Gly Leu Thr Leu Asn Cys Val Leu Leu Leu Gln Leu
 1               5                  10                  15

Leu Leu Ala Arg Ser Leu Glu Asp Gly Tyr Lys Val Glu Val Gly Lys
             20                  25                  30

Asn Ala Tyr Leu Pro Cys Ser Tyr Thr Leu Pro Thr Ser Gly Thr Leu
         35                  40                  45

Val Pro Met Cys Trp Gly Lys Gly Phe Cys Pro Trp Ser Gln Cys Thr
     50                  55                  60

Asn Glu Leu Leu Arg Thr Asp Glu Arg Asn Val Thr Tyr Gln Lys Ser
 65                  70                  75                  80

Ser Arg Tyr Gln Leu Lys Gly Asp Leu Asn Lys Gly Asp Val Ser Leu
                 85                  90                  95

Ile Ile Lys Asn Val Thr Leu Asp Asp His Gly Thr Tyr Cys Cys Arg
            100                 105                 110

Ile Gln Phe Pro Gly Leu Met Asn Asp Lys Lys Leu Glu Leu Lys Leu
        115                 120                 125

Asp Ile Lys Ala Ala Lys Val Thr Pro Ala Gln Thr His Gly Asp
    130                 135                 140

Ser Thr Thr Ala Ser Pro Arg Thr Leu Thr Thr Glu Arg Asn Gly Ser
145                 150                 155                 160

Glu Thr Gln Thr Leu Val Thr Leu His Asn Asn Gly Thr Lys Ile
                165                 170                 175

Ser Thr Trp Ala Asp Glu Ile Lys Asp Ser Gly Glu Thr Ile Arg Thr
            180                 185                 190

Ala Ile His Ile Gly Val Gly Val Ser Ala Gly Leu Thr Leu Ala Leu
        195                 200                 205

Ile Ile Gly Val Leu Ile Leu Lys Trp Tyr Ser Cys Lys Lys Lys Lys
    210                 215                 220
```

```
Leu Ser Ser Leu Ser Leu Ile Thr Leu Ala Asn Leu Pro Pro Gly Gly
225                 230                 235                 240

Leu Ala Asn Ala Gly Ala Val Arg Ile Arg Ser Glu Glu Asn Ile Tyr
                245                 250                 255

Thr Ile Glu Glu Asn Val Tyr Glu Val Glu Asn Ser Asn Glu Tyr Tyr
            260                 265                 270

Cys Tyr Val Asn Ser Gln Gln Pro Ser
        275                 280

<210> SEQ ID NO 3
<211> LENGTH: 1116
<212> TYPE: DNA
<213> ORGANISM: Homo sapiens

<400> SEQUENCE: 3
ggagagttaa aactgtgcct aacagaggtg tcctctgact tttcttctgc aagctccatg      60
ttttcacatc ttccctttga ctgtgtcctg ctgctgctgc tgctactact tacaaggtcc     120
tcagaagtgg aatacagagc ggaggtcggt cagaatgcct atctgccctg cttctacacc     180
ccagccgccc cagggaacct cgtgcccgtc tgctggggca aggagcctgt cctgtgtttt     240
gaatgtggca acgtggtgct caggactgat gaaagggatg tgaattattg acatccaga     300
tactggctaa atggggattt ccgcaaagga gatgtgtccc tgaccataga gaatgtgact     360
ctagcagaca gtgggatcta ctgctgccgg atccaaatcc caggcataat gaatgatgaa     420
aaatttaacc tgaagttggt catcaaacca gccaaggtca cccctgcacc gactctgcag     480
agagacttca ctgcagcctt tccaaggatg cttaccacca ggggacatgg cccagcagag     540
acacagacac tggggagcct ccctgatata aatctaacac aaatatccac attggccaat     600
gagttacggg actctagatt ggccaatgac ttacgggact ctggagcaac catcagaata     660
ggcatctaca tcggagcagg gatctgtgct gggctggctc tggctcttat cttcggcgct     720
ttaattttca atggtattc tcatagcaaa gagaagatac agaatttaag cctcatctct     780
ttggccaacc tccctccctc aggattggca aatgcagtag cagagggaat tcgctcagaa     840
gaaaacatct ataccattga agagaacgta tatgaagtgg aggagcccaa tgagtattat     900
tgctatgtca gcagcaggca gcaaccctca caacctttgg gttgtcgctt tgcaatgcca     960
tagatccaac caccttattt tgagcttggt gttttgtct ttttcagaaa ctatgagctg    1020
tgtcacctga ctggttttgg aggttctgtc cactgctatg gagcagagtt ttcccatttt    1080
cagaagataa tgactcacat ggaattgaa ctggga                              1116

<210> SEQ ID NO 4
<211> LENGTH: 301
<212> TYPE: PRT
<213> ORGANISM: Homo sapiens

<400> SEQUENCE: 4

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60
```

```
Asn Val Val Leu Arg Thr Asp Glu Arg Asp Val Asn Tyr Trp Thr Ser
 65                  70                  75                  80

Arg Tyr Trp Leu Asn Gly Asp Phe Arg Lys Gly Asp Val Ser Leu Thr
                 85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Leu Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Phe
    210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Gly Asn Val Tyr
            260                 265                 270

Glu Val Glu Glu Pro Asn Glu Tyr Tyr Cys Tyr Val Ser Ser Arg Gln
        275                 280                 285

Gln Pro Ser Gln Pro Leu Gly Cys Arg Phe Ala Met Pro
    290                 295                 300

<210> SEQ ID NO 5
<211> LENGTH: 1116
<212> TYPE: DNA
<213> ORGANISM: Homo sapiens

<400> SEQUENCE: 5
ggagagttaa aactgtgcct aacagaggtg tcctctgact tttcttctgc aagctccatg      60
ttttcacatc ttccctttga ctgtgtcctg ctgctgctgc tgctactact tacaaggtcc     120
tcagaagtgg aatacagagc ggaggtcggt cagaatgcct atctgccctg cttctacacc     180
ccagccgccc cagggaacct cgtgcccgtc tgctggggca aggagcctgt cctgtgtttt     240
gaatgtggca acgtggtgct caggactgat gaaaaggatg tgaattattg gacatccaga     300
tactggctaa atggggattt ccgcaaagga gatgtgtccc tgaccataga gaatgtgact     360
ctagcagaca gtgggatcta ctgctgccgg atccaaatcc caggcataat gaatgatgaa     420
aaatttaacc tgaagttggt catcaaacca gccaaggtca cccctgcacc gactcggcag     480
agagacttca ctgcagcctt tccaaggatg cttaccacca ggggacatgg cccagcagag     540
acacagacac tggggagcct ccctgatata aatctaacac aaatatccac attggccaat     600
gagttacggg actctagatt ggccaatgac ttacgggact ctggagcaac catcagaata     660
ggcatctaca tcggagcagg gatctgtgct gggctggctc tggctcttat cttcggcgct     720
ttaattttca atggtattc tcatagcaaa gagaagtac agaatttaag cctcatctct     780
```

-continued

| | |
|---|---|
| ttggccaacc tccctccctc aggattggca aatgcagtag cagagggaat tcgctcagaa | 840 |
| gaaaacatct ataccattga agagaacgta tatgaagtgg aggagcccaa tgagtattat | 900 |
| tgctatgtca gcagcaggca gcaaccctca caacctttgg gttgtcgctt tgcaatgcca | 960 |
| tagatccaac caccttatt ttgagcttgg tgttttgtct ttttcagaaa ctatgagctg | 1020 |
| tgtcacctga ctggttttgg aggttctgtc cactgctatg gagcagagtt ttcccatttt | 1080 |
| cagaagataa tgactcacat gggaattgaa ctggga | 1116 |

<210> SEQ ID NO 6
<211> LENGTH: 301
<212> TYPE: PRT
<213> ORGANISM: Homo sapiens

<400> SEQUENCE: 6

Met Phe Ser His Leu Pro Phe Asp Cys Val Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Phe
    210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
        275                 280                 285

Gln Pro Ser Gln Pro Leu Gly Cys Arg Phe Ala Met Pro
    290                 295                 300

<210> SEQ ID NO 7

```
<211> LENGTH: 7
<212> TYPE: PRT
<213> ORGANISM: Artificial sequence
<220> FEATURE:
<223> OTHER INFORMATION: Synthetic peptide

<400> SEQUENCE: 7

Arg Ser Glu Glu Asn Ile Tyr
1               5

<210> SEQ ID NO 8
<211> LENGTH: 13
<212> TYPE: PRT
<213> ORGANISM: Artificial sequence
<220> FEATURE:
<223> OTHER INFORMATION: Synthetic peptide

<400> SEQUENCE: 8

His Ser Leu Gly Lys Trp Leu Gly His Pro Asp Lys Phe
1               5                   10

<210> SEQ ID NO 9
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 9
caagccggtg gacctcagt                                                   19

<210> SEQ ID NO 10
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 10
agatgggagc cagcacag                                                    18

<210> SEQ ID NO 11
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 11
agctgcctgc ccagtgccct t                                                21

<210> SEQ ID NO 12
<211> LENGTH: 20
<212> TYPE: PRT
<213> ORGANISM: Artificial sequence
<220> FEATURE:
<223> OTHER INFORMATION: Synthetic peptide

<400> SEQUENCE: 12

Glu Ala Leu Val Arg Gln Gly Leu Ala Lys Val Ala Tyr Val Tyr Lys
1               5                   10                  15

Pro Asn Asn Thr
            20

<210> SEQ ID NO 13
<211> LENGTH: 197
```

```
<212> TYPE: PRT
<213> ORGANISM: Mus musculus

<400> SEQUENCE: 13

Met Phe Ser Gly Leu Thr Leu Asn Cys Val Leu Leu Leu Leu Gln Leu
1               5                   10                  15

Leu Leu Ala Arg Ser Leu Glu Asp Gly Tyr Lys Val Glu Val Gly Lys
                20                  25                  30

Asn Ala Tyr Leu Pro Cys Ser Tyr Thr Leu Pro Thr Ser Gly Thr Leu
            35                  40                  45

Val Pro Met Cys Trp Gly Lys Gly Phe Cys Pro Trp Ser Gln Cys Thr
        50                  55                  60

Asn Glu Leu Leu Arg Thr Asp Glu Arg Asn Val Thr Tyr Gln Lys Ser
65                  70                  75                  80

Ser Arg Tyr Gln Leu Lys Gly Asp Leu Asn Lys Gly Asp Val Ser Leu
                85                  90                  95

Ile Ile Lys Asn Val Thr Leu Asp Asp His Gly Thr Tyr Cys Cys Arg
            100                 105                 110

Ile Gln Phe Pro Gly Leu Met Asn Asp Lys Lys Leu Glu Leu Lys Leu
            115                 120                 125

Asp Ile Lys Ala Gly Tyr Ser Cys Lys Lys Lys Leu Ser Ser Leu
            130                 135                 140

Ser Leu Ile Thr Leu Ala Asn Leu Pro Pro Gly Gly Leu Ala Asn Ala
145                 150                 155                 160

Gly Ala Val Arg Ile Arg Ser Glu Glu Asn Ile Tyr Thr Ile Glu Glu
                165                 170                 175

Asn Val Tyr Glu Val Glu Asn Ser Asn Glu Tyr Tyr Cys Tyr Val Asn
            180                 185                 190

Ser Gln Gln Pro Ser
            195
```

US 9,962,440 B2

METHODS RELATED TO TIM 3, A TH1-SPECIFIC CELL SURFACE MOLECULE, FOR ACTIVATING ANTIGEN PRESENTING CELLS

CROSS-REFERENCED APPLICATIONS

This application is a Continuation application that claims benefit under 35 U.S.C. § 120 of U.S. application Ser. No. 14/185,050, filed Feb. 20, 2014, which is a Continuation application that claims benefit under 35 U.S.C. § 120 of U.S. application Ser. No. 13/331,387, filed Dec. 20, 2011, now U.S. Pat. No. 8,697,069, which is a Continuation application that claims benefit under 35 U.S.C. § 120 of U.S. application Ser. No. 12/276,977 filed Nov. 24, 2008, now U.S. Pat. No. 8,101,176, which is a Continuation application that claims benefit under 35 U.S.C. § 120 of U.S. application Ser. No. 10/354,447 filed Jan. 30, 2003, now U.S. Pat. No. 7,470,428, which claims the benefit under 35 U.S.C. § 119(e) of U.S. Provisional Application Ser. No. 60/353,107, filed Jan. 30, 2002, the contents of each of which are incorporated herein by reference in their entireties.

GOVERNMENT RIGHTS

This invention was funded in part under National Institutes of Health Grant Nos. R01-NS30843 and R01-NS38037. The United States government may retain certain rights in this invention.

SEQUENCE LISTING

The instant application contains a Sequence Listing which has been submitted in ASCII format via EFS-Web and is hereby incorporated by reference in its entirety. Said ASCII copy, created on Jan. 30, 2003 is named Seqlist.txt and is 17,776 bytes in size.

FIELD OF THE INVENTION

The present invention relates generally to compositions and methods useful for regulating the immune response. More particularly, the invention relates to methods of promoting and inhibiting immune effector cell function at the level of T-cell trafficking to target tissues and macrophage activation, both of which are disclosed herein to be related to functions of the Th1-specific cell surface molecule T cell Immunoglobulin and Mucin domain-containing molecule-3 (TIM-3). The invention also relates to methods of treating disorders such as cancer, infectious disease, allergy, asthma, and autoimmune disease.

BACKGROUND OF THE INVENTION

Activation of naïve CD4+ T helper cells results in the development of at least two distinct effector populations, Th1 cells and Th2 cells. Mosmann T R et al. (1986) *J Immunol* 136:2348-57; Mosmann T R et al. (1996) *Immunol Today* 17:138-46; Abbas A K et al. (1996) *Nature* 383:787-793. Th1 cells produce cytokines (interferon gamma (IFN-γ), interleukin-2 (IL-2), tumor necrosis factor alpha (TNF-α), and lymphotoxin) which are commonly associated with cell-mediated immune responses against intracellular pathogens, delayed-type hypersensitivity reactions (Sher A et al. (1992) *Annu Rev Immunol* 10:385-409), and induction of organ-specific autoimmune diseases. Liblau R S et al. (1995) *Immunol Today* 16:34-38. Th2 cells produce cytokines (IL-4, IL-10, and IL-13) that are crucial for control of extracellular helminthic infections and promote atopic and allergic diseases. Sher A et al. (1992) *Annu Rev Immunol* 10:385-409. In addition to their distinct roles in disease, the Th1 and Th2 cells cross-regulate each other's expansion and functions. Thus, preferential induction of Th2 cells inhibits autoimmune diseases (Kuchroo V K et al. (1995) *Cell* 80:707-18; Nicholson L B et al. (1995) *Immunity* 3:397-405), and predominant induction of Th1 cells can regulate induction of asthma, atopy and allergies. Lack G et al. (1994) *J Immunol* 152:2546-54; Hofstra C L et al. (1998) *J Immunol* 161:5054-60.

While much is known about the functions of these T-cell subsets, there are few known surface molecules that distinguish between them. Syrbe U et al. (1999) *Springer Semin Immunopathol* 21:263-85. Several groups have reported the association of certain chemokine and costimulatory molecule receptors with Th1 cells. Loetscher P et al. (1998) *Nature* 391:344-45; Bonecchi R et al. (1998) *J Exp Med* 187:129-34; Sallusto F et al. (1998) *J Exp Med* 187:875-83; Venkataraman C et al. (2000) *J Immunol* 165:632-36. Likewise, several groups have reported the association of certain chemokine and costimulatory molecule receptors with Th2 cells. Bonecchi R et al. (1998) *J Exp Med* 187:129-34; Sallusto F et al. (1998) *J Exp Med* 187:875-83; Jourdan P et al. (1998) *J Immunol* 160:4153-57; Zingoni A et al. (1998) *J Immunol* 161:547-51; McAdam A J et al. (2000) *J Immunol* 165:5035-40; Lohning M et al. (1998) *Proc Natl Acad Sci USA* 95:6930-35. However, the nature of the differences in expression of most of these molecules is quantitative.

U.S. Pat. No. 6,084,083, issued to Levinson discloses a murine Th1-restricted cell surface molecule termed the "200 gene product," along with its human homolog. The murine 200 gene product is there disclosed as a 280-amino acid membrane-bound member of the immunoglobulin (Ig) superfamily. The human homolog of the murine 200 gene product is there disclosed as a 301-amino acid membrane-bound member of the immunoglobulin (Ig) superfamily. Full-length nucleotide and amino acid sequences of the murine and human forms of the 200 gene and the 200 gene product, antibodies specific for the 200 gene product, and soluble forms of the 200 gene product are disclosed. Despite its identification as a Th1-restricted cell surface molecule, the function of the 200 gene and the endogenous ligand of the 200 gene are not disclosed in U.S. Pat. No. 6,084,083.

SUMMARY OF THE INVENTION

The present invention is based in part on the identification and structural and functional characterization of a transmembrane protein, TIM-3, which is preferentially expressed on differentiated Th1 cells. Full-length nucleotide and amino acid sequences of both human and murine forms of TIM-3 are disclosed. Comparison of these sequences with corresponding sequences of the independently discovered 200 genes and 200 gene products disclosed in U.S. Pat. No. 6,084,083 reveals their identity. Surprisingly, however, in vivo administration of antibody to TIM-3 enhances the clinical and pathologic severity of experimental autoimmune encephalomyelitis (EAE), a Th1-dependent autoimmune disease that is widely accepted as a model for multiple sclerosis, a demyelinating disorder in humans. In vivo administration of antibody to TIM-3 also increases the number and activation level of macrophages. TIM-3 may play an important role in the induction of autoimmune diseases by regulating macrophage activation and/or function. Thus TIM-3 plays an important role in the activation and expansion of macrophages in peripheral lymphoid tissue. As further disclosed herein, cognate interaction between T cells and macrophages is involved in this macrophage expansion and activation. The expansion and activation of macrophages is directed by the Th1 cells and is TIM-3-dependent.

The invention is also based in part on the unexpected finding that TIM-3 expression on effector Th1 cells promotes migration of Th1 cells to target tissues to mediate inflammation and immune response. As further disclosed herein, TIM-3-dependent trafficking of effector Th1 cells can be augmented with antibody to TIM-3 and inhibited with a soluble form of TIM-3.

Full-length TIM-3 is believed to be expressed as a membrane-associated protein having an extracellular region including an IgV domain and a mucin domain, a transmembrane region, and a cytoplasmic region. The invention is also based in part on the surprising discovery by the inventors of an alternatively spliced variant of TIM-3 in which the mucin domain and transmembrane region are deleted. This alternatively spliced variant of TIM-3 is believed to represent a naturally occurring form of soluble TIM-3.

In one aspect of the invention, a monoclonal antibody 8B.2C12 that binds specifically to TIM-3 is provided. Also provided in another aspect of the invention is a hybridoma 8B.2C12 that expresses the monoclonal antibody 8B.2C12.

In another aspect of the invention, the invention provides a monoclonal antibody 25F.1D6 that binds specifically to TIM-3. Also provided according to another aspect of the invention is a hybridoma 25F.1D6 that expresses the monoclonal antibody 25F.1D6.

In other aspects the invention provides pharmaceutical compositions containing the foregoing monoclonal antibodies specific for TIM-3. In one aspect the pharmaceutical composition includes monoclonal antibody 8B.2C12 and a pharmaceutically acceptable carrier. In another aspect the pharmaceutical composition includes monoclonal antibody 25F.1D6 and a pharmaceutically acceptable carrier.

Also provided are methods for preparing the pharmaceutical compositions containing the foregoing monoclonal antibodies specific for TIM-3. In one aspect the invention provides a method for preparing a pharmaceutical composition. The method involves placing monoclonal antibody 8B.2C12 in a pharmaceutically acceptable carrier. In another aspect the invention provides a method for preparing a pharmaceutical composition. The method involves placing monoclonal antibody 25F.1D6 in a pharmaceutically acceptable carrier.

In another aspect the invention provides a method for treating a subject in need of an enhanced immune response in a target tissue. The method involves administering to the subject a TIM-3-binding molecule in an effective amount to promote T-cell trafficking to the target tissue. In some embodiments the TIM-3-binding molecule is an antibody specific for TIM-3. In some embodiments the TIM-3-binding molecule is a fragment of an antibody specific for TIM-3.

In one embodiment the TIM-3-binding molecule is an antibody expressed by hybridoma 8B.2C12. In another embodiment the TIM-3-binding molecule is an antibody expressed by hybridoma 25F.1D6.

In some embodiments the TIM-3-binding molecule binds to an extracellular region of TIM-3. In accordance with the structure of TIM-3 as disclosed herein, in some embodiments the extracellular region of TIM-3 is an IgV domain or a fragment thereof, and in some embodiments the extracellular region of TIM-3 is a mucin domain or a fragment thereof.

In some preferred embodiments the subject has cancer or is at risk of having cancer. In some preferred embodiments the subject has an infection or is at risk of having an infection.

In some embodiments according to this aspect of the invention, the target tissue is selected from the group consisting of: brain, breast, lung, kidney, liver, pancreas, stomach, intestine, ovary, uterus, testis, prostate, marrow, bone, muscle, and skin. In one preferred embodiment, the target tissue is central nervous system.

In a preferred embodiment the subject is a human.

Also according to this aspect of the invention, in some embodiments the administering is to a site other than the target tissue. In some embodiments the administering is to a site other than a lymph node associated with the target tissue.

In some embodiments the administering is systemic. In a preferred embodiment the administering is intravenous.

Also according to this aspect of the invention, in some embodiments the method further entails administering to the subject an adjuvant.

In some embodiments the method according to this aspect of the invention further involves administering to the subject an anti-tumor medicament. In some preferred embodiments the anti-tumor medicament includes a tumor-specific antibody or tumor-specific fragment thereof.

Other agents can be administered as part of the method according to this aspect. For example, in some embodiments the method also includes administering to the subject a cytokine. In some embodiments the method according to this aspect of the invention further involves administering to the subject an antibacterial medicament. In some embodiments the method further involves administering to the subject an antiviral medicament. In some embodiments the method according to this aspect of the invention further involves administering to the subject an antifungal medicament. In some embodiments the method further involves administering to the subject an antiparasitic medicament.

In another aspect the invention provides a method for treating a subject in need of treatment for a tumor. The method according to this aspect involves administering to the subject a TIM-3-binding molecule in an effective amount to promote T-cell trafficking to the tumor.

In one embodiment the TIM-3-binding molecule is an antibody expressed by hybridoma 8B.2C12. In another embodiment the TIM-3-binding molecule is an antibody expressed by hybridoma 25F.1D6.

In another aspect the invention provides a method for treating a subject in need of treatment for an infection. The method according to this aspect involves administering to the subject a TIM-3-binding molecule in an effective amount to promote T-cell trafficking to the infection.

In one embodiment the TIM-3-binding molecule is an antibody expressed by hybridoma 8B.2C12. In another embodiment the TIM-3-binding molecule is an antibody expressed by hybridoma 25F.1D6.

In another aspect the invention provides a method for reducing T-cell trafficking into a target tissue of a subject. The method according to this aspect involves administering to the subject a TIM-3 ligand-binding molecule in an effective amount to reduce T-cell trafficking to a target tissue of the subject. In some embodiments the TIM-3 ligand-binding molecule includes at least one domain of an extracellular region of TIM-3. In one embodiment the at least one domain is an IgV domain. In some embodiments the TIM-3 ligand-binding molecule is soluble TIM-3. Preferably the soluble TIM-3 is a fusion protein including at least one domain of an extracellular region of TIM-3 and a constant heavy chain or portion thereof of an immunoglobulin. In one embodiment the at least one domain is an IgV domain.

In some embodiments the subject is in need of treatment for an autoimmune disease of the target tissue. In certain preferred embodiments the target tissue is selected from the group consisting of: central nervous system, pancreatic islets, and joint synovia. In certain preferred embodiments the autoimmune disease is selected from the group consisting of: multiple sclerosis, type 1 diabetes mellitus, and rheumatoid arthritis.

In yet another aspect the invention provides a method for treating or preventing asthma or allergy. The method according to this aspect of the invention involves increasing activity or expression of TIM-3 in a T cell of a subject to treat or prevent asthma or allergy. In one embodiment the T cell is a Th2 cell.

According to a further aspect, the invention provides a method for treating a Th2-mediated disorder in a subject. The method involves expressing TIM-3 on the surface of Th2 cells of a subject having a Th2-mediated disorder in an amount effective to treat the Th2-mediated disorder. In a preferred embodiment the Th2-mediated disorder is asthma.

In another aspect of the invention, a method is provided for promoting antigen-presenting cell (APC) activation. The method entails contacting an APC with a TIM-3 ligand-binding molecule in an effective amount to activate the APC.

In some embodiments the APC is a macrophage. In some embodiments the APC is a dendritic cell.

In some embodiments the TIM-3 ligand-binding molecule includes at least one domain of an extracellular region of TIM-3. In one embodiment the at least one domain is an IgV domain. In some embodiments the TIM-3 ligand-binding molecule is soluble TIM-3. Preferably the soluble TIM-3 is a fusion protein including at least one domain of an extracellular region of TIM-3 and a constant heavy chain or portion thereof of an immunoglobulin. In one embodiment the at least one domain is an IgV domain.

According to another aspect, the invention provides a method for promoting APC activation. The method according to this aspect involves contacting a T cell with a TIM-3-binding molecule, and contacting an APC with the T cell to activate the APC.

In some embodiments the APC is a macrophage. In some embodiments the APC is a dendritic cell.

In some embodiments the TIM-3-binding molecule is an antibody specific for TIM-3. In one embodiment the TIM-3-binding molecule is an antibody expressed by hybridoma 8B.2C12. In another embodiment the TIM-3-binding molecule is an antibody expressed by hybridoma 25F.1D6.

In some embodiments the TIM-3-binding molecule is a fragment of an antibody specific for TIM-3. In some embodiments the TIM-3-binding molecule binds to an extracellular region of TIM-3.

In some embodiments the method further includes contacting the T cell with an antigen specifically bound by a T-cell antigen receptor of the T cell.

In some embodiments the method further includes contacting the APC with an antibody specific for TIM-3.

In some embodiments according to this aspect of the invention, the contacting the APC with the T cell is ex vivo.

In one preferred embodiment the antigen is a tumor antigen.

According to yet another aspect of the invention, a method is provided for inhibiting APC activation. The method involves contacting an APC with an agent that reduces activity or expression of TIM-3 in an effective amount to inhibit activation of the APC.

In some embodiments the APC is a macrophage. In some embodiments the APC is a dendritic cell.

In some embodiments the agent that reduces activity or expression of TIM-3 is soluble TIM-3.

In some embodiments the agent that reduces activity or expression of TIM-3 includes at least one domain of an extracellular region of TIM-3. In one embodiment the at least one domain is an IgV domain.

In some embodiments the agent that reduces activity or expression of TIM-3 is a fusion protein including at least one domain of an extracellular region of TIM-3 and a constant heavy chain or portion thereof of an immunoglobulin. In one embodiment the at least one domain is an IgV domain.

In some embodiments the agent that reduces activity or expression of TIM-3 is an antisense polynucleotide capable of hybridization with a nucleic acid encoding TIM-3 under stringent hybridization conditions.

According to another aspect the invention further provides a method for treating or preventing intracellular infections. The method according to this aspect involves promoting macrophage activation by contacting a TIM-3 ligand on the macrophage with a TIM-3 expressing cell.

According to yet another aspect the invention provides a method for treating or preventing cancer. The method according to this aspect involves promoting APC activation by contacting a TIM-3 ligand on the APC with a TIM-3-expressing cell and contacting the APC with a cancer antigen.

BRIEF DESCRIPTION OF THE FIGURES

The following figures are provided for illustrative purposes only and are not required for understanding or practicing the invention.

FIGS. 4A and 4B show inflammatory/demyelinating lesions in the spinal cord of an anti-TIM-3 treated mouse on day 12 post-immunization at the peak of clinical disease. The infiltrate consists of a mixture of neutrophils and mononuclear cells. Perivascular fibrin deposition (arrow) indicates vasculitis and vascular injury. A portion of an intact peripheral nerve root (dark staining in FIG. 4B) is on the right side whereas most of the central nervous system (CNS) myelin in the field is lost. Mag.=411×. FIGS. 4C and 4D show extensive demyelination associated with a perivascular mononuclear cell infiltrate in the spinal cord posterior columns of an anti-TIM-3-treated mouse sacrificed on day 30 post-transfer. Inset (FIG. 4D): sheets of macrophages with phagocytosed myelin fragments (dark dots). Mag.=137×; inset=411×. FIGS. 4E and 4F show a similar infiltrate in the posterior columns of an isotype control mAb-treated mouse killed on day 30 post-immunization, with fewer macrophages and larger areas of intact (dark-staining) myelin. Mag.=137×. FIGS. 4A, 4C, and 4E, hematoxylin and eosin staining; FIGS. 4B, 4D, and 4F, Klüver-Barrera staining for myelin.

DETAILED DESCRIPTION OF THE INVENTION

The present invention is related to the novel appreciation of functional characteristics of a molecule that is selectively expressed on the surface of activated Th1 cells. The primary nucleotide and amino acid sequences of the particular molecule, here termed TIM-3, have previously been described in U.S. Pat. No. 6,084,083. It has been discovered according to the present invention that TIM-3 unexpectedly plays an important role in the activation and proliferation of macrophages. It has also been surprisingly discovered according to the present invention that TIM-3-dependent activation and expansion of macrophages involves a cognate interaction between the T cell expressing TIM-3 and the macrophage. Consistent with this finding, it has further been discovered according to the present invention that antigen-presenting cells (APCs), including macrophages and dendritic cells, express a ligand or receptor for TIM-3.

It has been discovered according to the present invention that molecules that bind to TIM-3, such as antibodies directed to TIM-3, can, surprisingly, induce macrophage activation and proliferation. The macrophage activation induced by binding molecules directed against TIM-3 promotes migration of the macrophages into target tissues, including tissue within the central nervous system (CNS). For example, it has been discovered according to the present invention that treatment with anti-TIM-3 of mice that are genetically susceptible of developing experimental allergic encephalomyelitis (EAE), an in vivo model for multiple sclerosis, a Th1-type autoimmune disease of the brain in humans, results in an unusually severe form of EAE characterized by massive infiltration of activated macrophages into the CNS. Thus administration of antibodies directed against TIM-3 unexpectedly exacerbated, rather than ameliorated, this autoimmune disease.

Accordingly, in some aspects the present invention provides methods that are useful for promoting APC activation, e.g., in treating or preventing intracellular infection, cancer, and autoimmune disease.

It has further been surprisingly discovered according to the present invention that TIM-3 expression on effector Th1 cells promotes trafficking of Th1 cells to target tissues. Unexpectedly, TIM-3-dependent trafficking of Th1 cells to target tissue can be augmented with antibody for TIM-3.

Thus in some aspects the present invention provides methods that are useful for promoting T-cell trafficking into a target tissue, e.g., in subjects in need of an enhanced immune response in the target tissue.

Furthermore, and importantly, it has surprisingly been discovered according to the instant invention that TIM-3-dependent trafficking of Th1 cells to target tissue can be inhibited with soluble TIM-3. Thus in some other aspects the present invention provides methods that are useful for reducing T-cell trafficking into a target tissue, e.g., in subjects with autoimmune disease.

Figure 1A:
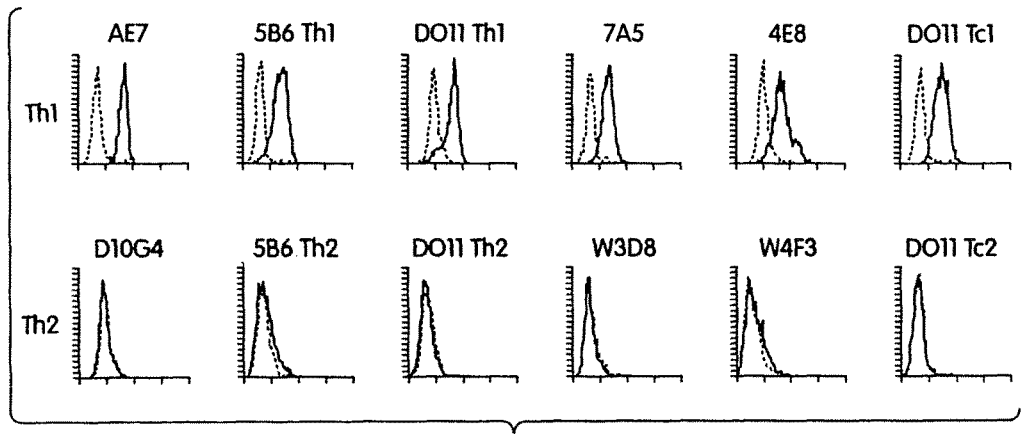
FIG. 1A is a series of graphs depicting flow cytometric analyses of various indicated cell types for expression of TIM-3. Th1, Th2, Tc1 and Tc2 cells were stained with rat monoclonal antibody (mAb) to TIM-3 (solid line) or isotype control (dotted line).
Figure 1B:
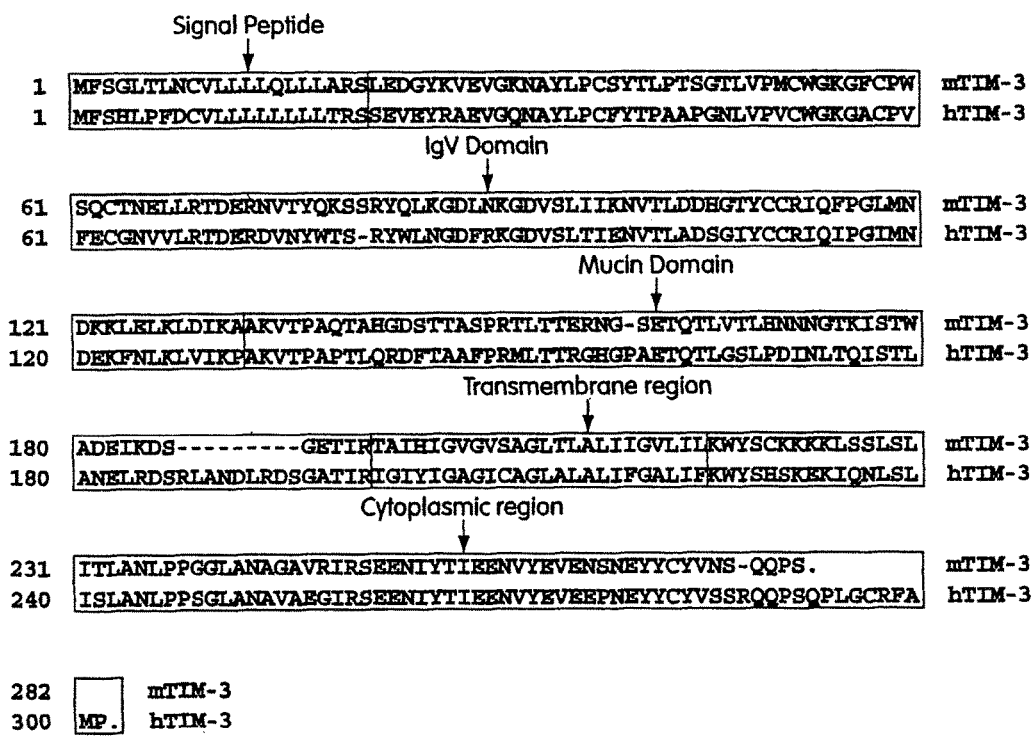
FIG. 1B is a graphical representation and comparison of deduced amino acid sequences of murine TIM-3 (mTIM-3; SEQ ID NO:2) and human TIM-3 (hTIM-3; SEQ ID NO:4), pointing out the IgV-like domain, mucin domain, transmembrane region, and cytoplasmic region for each.

As used herein, "TIM-3" refers to the gene product encoded by the nucleotide sequence of SEQ ID NO:1 (murine), SEQ ID NO:3 (human), as well as homologs, alleles, and functional variants thereof, e.g., SEQ ID NO:5. The gene product corresponding to the murine nucleotide sequence of SEQ ID NO:1 is SEQ ID NO:2. The gene product corresponding to the human nucleotide sequence of SEQ ID NO:3 is SEQ ID NO:4; the gene product corresponding to the human nucleotide sequence of SEQ ID NO:5 is SEQ ID NO:6. The nucleotide sequence of SEQ ID NO:3 differs from that of independently determined SEQ ID NO:5 at one base, 476 (T in SEQ ID NO:3 and G in SEQ ID NO:5). This single nucleotide difference results in a change of encoded amino acid from L (leucine) in SEQ ID NO:4 to R (arginine) in SEQ ID NO:6 at position 140. As shown in FIG. 1B, TIM-3 is a transmembrane protein that includes an extracellular region (including a signal peptide, an IgV domain, and a mucin domain, each as described further below), a transmembrane region, and a cytoplasmic region. Normally TIM-3 is preferentially expressed on the surface of activated Th1 cells. TIM-3 cDNA sequences of the instant invention have been deposited at the GenBank database under accession numbers AF450241-AF450243, shown below as SEQ ID NOs:1, 3, and 5, respectively. TIM-3 amino acid sequences of the instant invention have been deposited at the GenBank database under accession numbers AAL65156-AAL65158, shown below as SEQ ID NOs:2, 4, and 6, respectively.

```
Nucleotide sequence of murine TIM-3 cDNA
GenBank Accession No. AF450241
                                                              SEQ ID NO: 1
ttttaaccga ggagctaaag ctatccctac acagagctgt ccttggattt ccctgccaa    60 gtactcatgt tttcaggtct taccctcaac tgtgtcctgc tgctgctgca actactactt   120
gcaaggtcat tggaagatgg ttataaggtt gaggttggta aaaatgccta tctgccctgc   180
agttacactc tacctacatc tgggacactt gtgcctatgt gctgggcaa gggattctgt    240 ccttggtcac agtgtaccaa tgagttgctc agaactgatg aaagaaatgt gacatatcag   300
aaatccagca gataccagct aaagggcgat ctcaacaaag gagatgtgtc tctgatcata   360
aagaatgtga ctctggatga ccatgggacc tactgctgca ggatacagtt ccctggtctt   420
atgaatgata aaaaattaga actgaaatta gacatcaaag cagccaaggt cactccagct   480
cagactgccc atggggactc tactacagct tctccaagaa ccctaaccac ggagagaaat   540
ggttcagaga cacagacact ggtgaccctc cataataaca atggaacaaa aatttccaca   600
tgggctgatg aaattaagga ctctggagaa acgatcagaa ctgctatcca cattggagtg   660
ggagtctctg ctgggttgac cctggcactt atcattggtg tcttaatcct taaatggtat   720
tcctgtaaga aaaagaagtt atcgagtttg agccttatta cactggccaa cttgcctcca   780
ggagggttgg caaatgcagg agcagtcagg attcgctctg aggaaaatat ctacaccatc   840
gaggagaacg tatatgaagt ggagaattca aatgagtact actgctacgt caacagccag   900
cagccatcct gaccgcctct ggactgccac ttttaaaggc tcgccttcat ttctgacttt   960
ggtatttccc tttttgaaaa ctatgtgata tgtcacttgg caacctcatt ggaggttctg  1020
accacagcca ctgagaaaag agttccagtt ttctgggat aattaactca caagggatt   1080 cgactgtaac tcatgctaca ttgaaatgct ccattttatc cctgagtttc agggatcgga  1140
tctcccactc cagagacttc aatcatgcgt gttgaagctc actcgtgctt tcatacatta  1200
ggaatggtta gtgtgatgtc tttgagacat agaggtttgt ggtatatccg caaagctcct  1260
gaacaggtag ggggaataaa gggctaagat aggaaggtgc ggttctttgt tgatgttgaa  1320
aatctaaaga agttggtagc ttttctagag atttctgacc ttgaaagatt aagaaaaagc  1380
caggtggcat atgcttaaca cgatataact tgggaacctt aggcaggagg gtgataagtt  1440
caaggtcagc cagggctatg ctggtaagac tgtctcaaaa tccaaagacg aaaataaaca  1500
tagagacagc aggaggctgg agatgaggct cggacagtga ggtgcatttt gtacaagcac  1560
```

-continued

```
gaggaatcta tatttgatcg tagacccac atgaaaaagc taggcctggt agagcatgct 1620
tgtagactca agagatggag aggtaaaggc acaacagatc cccggggctt gcgtgcagtc 1680
agcttagcct aggtgctgag ttccaagtcc acaagagtcc ctgtctcaaa gtaagatgga 1740
ctgagtatct ggcgaatgtc catgggggtt gtcctctgct ctcagaagag acatgcacat 1800
gaacctgcac acacacacac acacacacac acacacacac acacacacac acacatgaaa 1860
tgaaggttct ctctgtgcct gctacctctc tataacatgt atctctacag gactctcctc 1920
tgcctctgtt aagacatgag tgggagcatg gcagagcagt ccagtaatta attccagcac 1980
tcagaaggct ggagcagaag cgtggagagt tcaggagcac tgtgcccaac actgccagac 2040
tcttcttaca caagaaaaag gttacccgca agcagcctgc tgtctgtaaa aggaaaccct 2100
gcgaaaggca aactttgact gttgtgtgct caagggaaac tgactcagac aacttctcca 2160
ttcctggagg aaactggagc tgtttctgac agaagaacaa ccggtgactg ggacatacga 2220
aggcagagct cttgcagcaa tctatatagt cagcaaaata ttctttggga ggacagtcgt 2280
caccaaattg atttccaagc cggtggacct cagtttcatc tggcttacag ctgcctgccc 2340
agtgcccttg atctgtgctg gctcccatct ataacagaat caaattaaat agaccccgag 2400
tgaaaatatt aagtgagcag aaaggtagct ttgttcaaag atttttttgc attggggagc 2460
aactgtgtac atcagaggac atctgttagt gaggacacca aaacctgtgg taccgttttt 2520
tcatgtatga attttgttgt ttaggttgct tctagctagc tgtggaggtc ctggcttttct 2580 taggtgggta tggaagggag accatctaac aaaatccatt agagataaca gctctcatgc 2640
agaagggaaa actaatctca aatgttttaa agtaataaaa ctgtactggc aaagtacttt 2700
gagcatattt aaaaaaaaaa aaaaa                                       2725
```

Nucleotide sequence of human TIM-3 cDNA, clone 1
GenBank Accession No. AF450242

SEQ ID NO: 3

```
ggagagttaa aactgtgcct aacagaggtg tcctctgact tttcttctgc aagctccatg   60
ttttcacatc ttccctttga ctgtgtcctg ctgctgctgc tgctactact tacaaggtcc  120
tcagaagtgg aatacagagc ggaggtcggt cagaatgcct atctgccctg cttctacacc  180
ccagccgccc cagggaacct cgtgccgtc tgctggggca aggagcctg tcctgtgttt  240 gaatgtggca acgtggtgct caggactgat gaaagggatg tgaattattg acatccaga   300 tactggctaa atgggatttc cgcaaagga gatgtgtccc tgaccataga gaatgtgact   360
ctagcagaca gtgggatcta ctgctgccgg atccaaatcc caggcataat gaatgatgaa   420
aaatttaacc tgaagttggt catcaaacca gccaaggtca cccctgcacc gactctgcag   480
agagacttca ctgcagccct tccaaggatg cttaccacca ggggacatgg cccagcagag  540
acacagacac tggggagcct ccctgatata aatctaacac aaatatccac attggccaat  600
gagttacggg actctagatt ggccaatgac ttacgggact ctggagcaac catcagaata   660
ggcatctaca tcggagcagg gatctgtgct gggctggctc tggctcttat cttcggcgct   720 ttaatttca atggtattc tcatagcaaa gagaagatac agaatttaag cctcatctct   780
ttggccaacc tccctccctc aggattggca aatgcagtag cagagggaat cgctcagaa   840 gaaaacatct ataccattga agagaacgta tatgaagtgg aggagcccaa tgagtattat  900
tgctatgtca gcagcaggca gcaaccctca caacctttgg gttgtcgctt tgcaatgcca   960
tagatccaac caccttattt ttgagcttgg tgttttgtct tttcagaaa ctatgagctg 1020 tgtcacctga ctggttttgg aggttctgtc cactgctatg gagcagagtt ttcccatttt 1080
cagaagataa tgactcacat gggaattgaa ctgggga                           1116
```

-continued

Nucleotide sequence of human TIM-3 cDNA, clone 2
GenBank Accession No. AF450243

SEQ ID NO: 5

```
ggagagttaa aactgtgcct aacagaggtg tcctctgact tttcttctgc aagctccatg   60
ttttcacatc ttcccttttga ctgtgtcctg ctgctgctgc tgctactact tacaaggtcc  120
tcagaagtgg aatacagagc ggaggtcggt cagaatgcct atctgccctg cttctacacc  180
ccagccgccc cagggaacct cgtgcccgtc tgctggggca aggagcctg tcctgtgttt   240
gaatgtggca acgtggtgct caggactgat gaaagggatg tgaattattg gacatccaga  300
tactggctaa atgggatttt ccgcaaagga gatgtgtccc tgaccataga gaatgtgact  360
ctagcagaca gtgggatcta ctgctgccgg atccaaatcc caggcataat gaatgatgaa  420
aaatttaacc tgaagttggt catcaaacca gccaaggtca cccctgcacc gactctgcag  480
agagacttca ctgcagcctt tccaaggatg cttaccacca ggggacatgg cccagcagag  540
acacagacac tggggagcct ccctgatata aatctaacac aaatatccac attggccaat  600
gagttacggg actctagatt ggccaatgac ttacgggact ctggagcaac catcagaata  660
ggcatctaca tcggagcagg gatctgtgct gggctggctc tggctcttat cttcggcgct  720
ttaattttca atggtattc tcatagcaaa gagaagatac agaatttaag cctcatctct  780
ttggccaacc tccctcccte aggattggca aatgcagtag cagagggaat tcgctcagaa  840
gaaaacatct ataccattga agagaacgta tatgaagtgg aggagcccaa tgagtattat  900
tgctatgtca gcagcaggca gcaacccctca caacctttgg gttgtcgctt tgcaatgcca  960
tagatccaac caccttattt ttgagcttgg tgttttgtct ttttcagaaa ctatgagctg 1020
tgtcacctga ctggttttgg aggttctgtc cactgctatg agcagagtt ttcccatttt 1080
cagaagataa tgactcacat gggaattgaa ctggga                           1116
```

Amino acid sequence of murine TIM-3
GenBank Accession No. AAL65156

SEQ ID NO: 2

```
MFSGLTLNCV LLLLQLLLAR SLEDGYKVEV GKNAYLPCSY TLPTSGTLVP MCWGKGFCPW   60
SQCTNELLRT DERNVTYQKS SRYQLKGDLN KGDVSLIIKN VTLDDHGTYC CRIQFPGLMN  120
DKKLELKLDI KAAKVTPAQT AHGDSTTASP RTLTTERNGS ETQTLVTLHN NNGTKISTWA  180
DEIKDSGETI RTAIHIGVGV SAGLTLALII GVLILKWYSC KKKKLSSLSL ITLANLPPGG  240
LANAGAVRIR SEENIYTIEE NVYEVENSNE YYCYVNSQQP S                     281
```

Amino acid sequence of human TIM-3, clone 1
GenBank Accession No. AAL65157

SEQ ID NO: 4

```
MFSHLPFDCV LLLLLLLLTR SSEVEYRAEV GQNAYLPCFY TPAAPGNLVP VCWGKGACPV   60
FECGNVVLRT DERDVNYWTS RYWLNGDFRK GDVSLTIENV TLADSGIYCC RIQIPGIMND  120
EKFNLKLVIK PAKVTPAPTL QRDFTAAFPR MLTTRGHGPA ETQTLGSLPD INLTQISTLA  180
NELRDSRLAN DLRDSGATIR IGIYIGAGIC AGLALALIFG ALIFKWYSHS KEKIQNLSLI  240
SLANLPPSGL ANAVAEGIRS EENIYTIEEN VYEVEEPNEY YCYVSSRQQP SQPLGCRFAM  300
P                                                                 301
```

Amino acid sequence of human TIM-3, clone 2
GenBank Accession No. AAL65158

SEQ ID NO: 6

```
MFSHLPFDCV LLLLLLLLTR SSEVEYRAEV GQNAYLPCFY TPAAPGNLVP VCWGKGACPV   60
FECGNVVLRT DERDVNYWTS RYWLNGDFRK GDVSLTIENV TLADSGIYCC RIQIPGIMND  120
EKFNLKLVIK PAKVTPAPTR QRDFTAAFPR MLTTRGHGPA ETQTLGSLPD INLTQISTLA  180
```

```
-continued

NELRDSRLAN DLRDSGATIR IGIYIGAGIC AGLALALIFG ALIFKWYSHS KEKIQNLSLI    240

SLANLPPSGL ANAVAEGIRS EENIYTIEEN VYEVEEPNEY YCYVSSRQQP SQPLGCRFAM    300

P                                                                  301
```

Functional variants of TIM-3 include molecules representing mutations, additions, deletions, and truncations of full-length TIM-3, provided such molecules retain at least one functional characteristic of full-length TIM-3. For example, a TIM-3 molecule truncated so as to lack most or all of its cytoplasmic domain is expected to retain the ability to bind to ligands or receptors for TIM-3.

Certain aspects of the invention involve methods which promote T-cell trafficking into selected tissues.

In one aspect the invention provides a method for treating a subject in need of an enhanced immune response in a target tissue. The method involves administering to the subject a TIM-3-binding molecule in an effective amount to promote T-cell trafficking to the target tissue.

In another aspect the invention provides a method for treating a subject in need of treatment for a tumor. The method according to this aspect of the invention involves administering to a subject in need of treatment for a tumor a TIM-3-binding molecule in an effective amount to promote T-cell trafficking to the tumor.

In yet another aspect the invention provides a method for treating a subject in need of treatment for an infection. The method according to this aspect of the invention involves administering to a subject in need of treatment for an infection a TIM-3-binding molecule in an effective amount to promote T-cell trafficking to the infection.

As used herein, "treat" and "treating" refer to a therapeutic intervention in a subject to prevent the onset of, alleviate the symptoms of, or slow or stop the progression of a disorder or disease being treated in the subject. The therapeutic intervention can be the administration of a therapeutically effective amount of a substance to prevent the onset of, alleviate the symptoms of, or slow or stop the progression of a disorder or disease being treated.

A "subject" as used herein refers to any vertebrate animal, preferably a mammal, and more preferably a human. Examples of subjects include humans, non-human primates, rodents, guinea pigs, rabbits, sheep, pigs, goats, cows, horses, dogs, cats, birds, and fish.

A "subject in need of an enhanced immune response" as used herein refers to a subject having or at risk of having a disease, disorder, or condition that is associated with a deficient or absent immune response, or that can be relieved by augmenting an immune response. Subjects in need of an enhanced immune response are common and are readily recognized by those of skill in the art. The very young, the elderly, subjects with chronic disease or acute-on-chronic disease, subjects with susceptibility to infection due to compromised barriers to infection (including subjects with cystic fibrosis), subjects with drug-induced immune deficiency, critically ill subjects, subjects about to undergo surgery, subjects with congenital or genetic forms of immunodeficiency, subjects with acquired forms of immunodeficiency (including subjects infected with human immunodeficiency virus, HIV), subjects with persistent infection, subjects with intracellular infection, and subjects with cancer are all subjects in need of an enhanced immune response. This list is meant to be representative and not limiting in any way.

A "target tissue" as used herein refers to a tissue representing a site of immune effector activity. A target tissue can be any tissue in a subject. Examples of target tissues include brain or central nervous system, breast, lung, kidney, liver, pancreas (including in particular pancreatic islets), stomach, intestine, ovary, uterus, testis, prostate, marrow, bone, joint synovia, muscle, and skin. Typically, target tissues are tissues not primarily associated with lymphoid tissues, except in situations involving cancers, infections, and inflammatory conditions of those tissues. Thus target tissues can, but typically do not, include lymph nodes, spleen, mucosal lymphoid tissues (including, e.g., Peyer's patches), or thymus.

As used herein, a "TIM-3-binding molecule" is any molecule that binds specifically to TIM-3. The TIM-3-binding molecule can be a small molecule, a polypeptide, an antibody or a fragment of an antibody, a polynucleotide, a carbohydrate including a polysaccharide, a lipid, a drug, as well as mimics, derivatives, and combinations thereof. The TIM-3-binding molecule can be found in nature or it can be derived or synthesized using suitable in vitro and synthetic methods known by those of skill in the art. For example, the TIM-3-binding molecule can be a small molecule that is identified through screening a library of small molecules for the ability to bind to TIM-3.

The TIM-3-binding molecule can be generated and identified using phage display of peptides. As yet another example, the TIM-3-binding molecule can be a TIM-3 ligand, including a soluble TIM-3 ligand. A "TIM-3 ligand" as used herein refers to a type of TIM-3-binding molecule that binds specifically to the extracellular region of TIM-3. TIM-3 ligand is a naturally occurring receptor or counter-receptor for TIM-3, and it is believed to be expressed on certain cells of the immune system, including macrophages and dendritic cells. It is also believed that TIM-3 ligand can also be expressed on certain other cells that come in contact with TIM-3 expressed on T cells, e.g., endothelial cells, mucosal epithelial cells, and the like. Engagement of TIM-3 ligand by TIM-3 can deliver a signal to the interior of the cell expressing TIM-3 ligand on its surface and/or the cell expressing TIM-3 on its surface. A TIM-3 ligand also refers to any TIM-3-binding molecule that competes with a naturally occurring TIM-3 ligand for binding to TIM-3. A TIM-3 ligand thus includes but is not limited to a naturally occurring TIM-3 ligand that binds to TIM-3.

"Soluble TIM-3 ligand" refers to any form of TIM-3 ligand that is dissociated from cell membrane. Soluble TIM-3 ligand can be a C-terminal truncated form of full-length TIM-3 ligand or a transmembrane-deleted version of TIM-3 ligand. In one embodiment soluble TIM-3 ligand refers to a fusion protein that includes at least an extracellular domain of TIM-3 ligand and another polypeptide. In one embodiment the soluble TIM-3 ligand is a fusion protein including the extracellular region of TIM-3 ligand covalently linked, e.g., via a peptide bond, to an Fc fragment of an immunoglobulin such as IgG.

In some embodiments the TIM-3-binding molecule is an antibody specific for TIM-3 or is a fragment of an antibody specific for TIM-3. An "antibody specific for TIM-3" as used herein refers to an immunoglobulin that binds specifically to a TIM-3 epitope through interaction between the epitope and a variable domain of the immunoglobulin. A "fragment of an antibody specific for TIM-3" shall refer to a portion of an intact antibody specific for TIM-3 that binds specifically to a TIM-3 epitope through interaction between the epitope and a variable domain of the intact immunoglobulin from which the fragment is derived. A "fragment of an antibody specific for TIM-3" shall also refer to an engineered equivalent of a portion of an intact antibody specific for TIM-3 that binds specifically to a TIM-3 epitope through interaction between the epitope and a variable domain. As is well known in the art, intact antibodies generally include both variable domains and at least one constant domain. The variable domain includes contributions from heavy and light chains that together provide stretches of contact residues specific for the binding of the antibody with an antigen. The constant domain is not specific for the antigen but rather is more or less common to all antibodies of a particular isotype; it may be involved in binding complement or antigen-independent binding of the antibody to Fc receptors expressed on certain immune effector cells. The antibody can be monoclonal or polyclonal. Furthermore, the antibody can be native or it can be engineered in part or in whole to reduce its potential immunogenicity in a treated host. Methods for generating and isolating polyclonal and monoclonal antibodies specific for a given antigen are well described in the art. See, for example, Kohler and Milstein (1975) Nature 256:495-7; Harlow and Lane, *Antibodies: A Laboratory Manual*, Cold Spring Harbor, N.Y., current edition.

The antibody specific for TIM-3 is meant to encompass antibodies derived from any appropriate species. For example, antibodies for a particular antigen can be raised by immunizing an appropriate host with the antigen. The immunized host can be selected from a variety of species, including, for example, mouse, rat, hamster, guinea pig, rabbit, goat, sheep, horse, monkey, and human. Methods for generating chimeric and humanized monoclonal antibodies are also well known in the art, and examples of such antibodies are in clinical use today. In addition to the species of origin of the antibody, those of skill in the art recognize that various isotypes or classes of immunoglobulin exist. These include, for example, IgG, IgA, IgE, IgM, and IgD. Within these classes there can also be further subclasses or subtypes, e.g., human IgG subtypes include IgG1, IgG2, IgG3, and IgG4, while murine IgG subtypes include IgG1, IgG2a, IgG2b, and IgG3. The antibody specific for TIM-3 is meant to encompass any isotype and subtype. In some embodiments the antibody is an IgG.

In some embodiments the TIM-3-binding molecule binds to an extracellular region of TIM-3. The term "extracellular region of TIM-3" refers to that portion of the expressed TIM-3 gene product that normally resides substantially on the extracellular surface of a cell expressing the TIM-3 gene product. In accordance with the present invention, the predicted amino acid sequence of TIM-3 includes an extracellular region, a transmembrane region, and a cytoplasmic or intracellular region. The extracellular region is predicted to include the N-terminal 191 amino acid residues of murine TIM-3 and the N-terminal 200 amino acid residues of human TIM-3, inclusive of a 21 amino acid signal peptide in each instance. The signal peptide can be cleaved from the expressed protein product so that the extracellular region of murine TIM-3 is 170 amino acids long and the extracellular region of human TIM-3 is 179 amino acids long.

The extracellular region of TIM-3 is believed to include at least two domains, an IgV domain and a mucin domain (see FIG. 1B). The IgV domain of TIM-3 shares structural similarities with an immunoglobulin variable domain, and it is believed to occupy amino acids 22-132 in murine TIM-3 and amino acids 22-131 in human TIM-3. The mucin domain is believed to occupy amino acids 133-191 in murine TIM-3 and amino acids 132-200 in human TIM-3.

As used herein, the expression "IgV domain or a fragment thereof" refers to the full-length IgV domain of the extracellular region of TIM-3 or to a portion of the full-length IgV domain of the extracellular region of TIM-3 sufficiently long to be used as an antigen for immunization of a host. It is generally believed that a linear determinant of a protein antigen that forms contacts with a specific antibody is about six amino acids long. Thus typically the fragment will include at least six contiguous amino acids according to SEQ ID NO:2 or SEQ ID NO:4 included in the IgV domain as specified above.

As used herein, the term "mucin domain or a fragment thereof" refers to the full-length mucin domain of the extracellular region of TIM-3 or to a portion of the full-length mucin domain of the extracellular region of TIM-3 sufficiently long to be used as an antigen for immunization of a host. A fragment will typically include at least six contiguous amino acids according to SEQ ID NO:2 or SEQ ID NO:4 included in the mucin domain as specified above.

An "effective amount" as used herein is any amount that is sufficient either to promote the occurrence of a desired outcome or condition, or to reduce or inhibit the occurrence of an undesired outcome or condition. In some instances a desired outcome or condition is an ideal that represents one end of a spectrum of possible outcomes or conditions. In such instances an effective amount is any amount associated with an outcome or condition that is closer to the desired ideal than would be achieved or observed without the effective amount. Thus an effective amount promotes the occurrence of a desired outcome or condition, but it need not achieve an ultimate endpoint.

As used herein, "T-cell trafficking" refers to migration of T lymphocytes to a site of immune response activity. Naïve T cells recirculate throughout the body, leaving and reentering the lymphoid tissues as they sample their environment for the presence of non-self antigens or "danger" signals. Lymphoid tissues are specially adapted to help promote encounters between antigen-specific T-cell receptors expressed on T cells and their cognate antigens. Specialized antigen-presenting cells (APCs) concentrate within lymphoid tissues, and are specially adapted to interact with and to present antigens to T cells to initiate an immune response by T cells genetically programmed to recognize a particular antigen. Following T-cell activation in response to encounter with specific antigen, T cells proliferate, undergo differentiation to produce a variety of secreted and cell-associated products, including cytokines, and migrate to tissue sites associated with the antigen. The result of this process is that naïve T cells circulate randomly while activated T cells proliferate and home to specific tissue sites.

In some embodiments the subject has cancer or is at risk of having cancer. A "cancer" as used herein refers to an uncontrolled growth of cells which interferes with the normal functioning of the bodily organs and systems. A subject that has a cancer is a subject having objectively measurable cancer cells present in the subject's body. A subject at risk of having a cancer is a subject that is predisposed to develop a cancer. Such a subject can include, for example, a subject with a family history of or a genetic predisposition toward developing a cancer. A subject at risk of having a cancer also can include a subject with a known or suspected exposure to a cancer-causing agent.

Cancers which migrate from their original location and seed vital organs can eventually lead to the death of the subject through the functional deterioration of the affected organs. Hemopoietic cancers, such as leukemia, are able to out-compete the normal hemopoietic compartments in a subject, thereby leading to hemopoietic failure (in the form of anemia, thrombocytopenia and neutropenia) ultimately causing death.

A metastasis is a region of cancer cells, distinct from the primary tumor location resulting from the dissemination of cancer cells from the primary tumor to other parts of the body. At the time of diagnosis of the primary tumor mass, the subject may be monitored for the presence of metastases. Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

Cancers include, but are not limited to, basal cell carcinoma; biliary tract cancer; bladder cancer; bone cancer; brain and CNS cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia; liver cancer; lung cancer (e.g., small cell and non-small cell); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; sarcoma; skin cancer; stomach cancer; testicular cancer; thyroid cancer; uterine cancer; cancer of the urinary system, as well as other carcinomas and sarcomas.

In some preferred embodiments the subject has an infection or is at risk of having an infection. An "infection" as used herein refers to a disease or condition attributable to the presence in a host of a foreign organism or agent that reproduces within the host. Infections typically involve breach of a normal mucosal or other tissue barrier by an infectious organism or agent. A subject that has an infection is a subject having objectively measurable infectious organisms or agents present in the subject's body. A subject at risk of having an infection is a subject that is predisposed to develop an infection. Such a subject can include, for example, a subject with a known or suspected exposure to an infectious organism or agent. A subject at risk of having an infection also can include a subject with a condition associated with impaired ability to mount an immune response to an infectious organism or agent, e.g., a subject with a congenital or acquired immunodeficiency, a subject undergoing radiation therapy or chemotherapy, a subject with a burn injury, a subject with a traumatic injury, a subject undergoing surgery or other invasive medical or dental procedure.

Infections are broadly classified as bacterial, viral, fungal, or parasitic based on the category of infectious organism or agent involved. Other less common types of infection are also known in the art, including, e.g., infections involving rickettsiae, mycoplasmas, and agents causing scrapie, bovine spongiform encephalopthy (BSE), and prion diseases (e.g., kuru and Creutzfeldt-Jacob disease). Examples of bacteria, viruses, fungi, and parasites which cause infection are well known in the art. An infection can be acute, subacute, chronic, or latent, and it can be localized or systemic. Furthermore, an infection can be predominantly intracellular or extracellular during at least one phase of the infectious organism's or agent's life cycle in the host.

Bacteria include both Gram negative and Gram positive bacteria. Examples of Gram positive bacteria include, but are not limited to *Pasteurella* species, Staphylococci species, and *Streptococcus* species. Examples of Gram negative bacteria include, but are not limited to, *Escherichia coli*, *Pseudomonas* species, and *Salmonella* species. Specific examples of infectious bacteria include but are not limited to: *Helicobacter pyloris, Borrelia burgdorferi, Legionella pneumophilia, Mycobacteria* spp. (e.g., *M. tuberculosis, M. avium, M. intracellulare, M. kansasii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic spp.), *Streptococcus pneumoniae*, pathogenic *Campylobacter* spp., *Enterococcus* spp., *Haemophilus influenzae, Bacillus anthracis, Corynebacterium diphtheriae, Corynebacterium* spp., *Erysipelothrix rhusiopathiae, Clostridium perfringens, Clostridium tetani, Enterobacter aerogenes, Klebsiella pneumoniae, Pasturella multocida, Bacteroides* spp., *Fusobacterium nucleatum, Streptobacillus moniliformis, Treponema pallidum, Treponema pertenue, Leptospira, Rickettsia*, and *Actinomyces israelii*.

Examples of virus that have been found to cause infections in humans include but are not limited to: Retroviridae (e.g., human immunodeficiency viruses, such as HIV-1 (also referred to as HTLV-III), HIV-2, LAV or HTLV-III/LAV, or HIV-III, and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=enterally transmitted; class 2=parenterally transmitted (i.e., Hepatitis C); Norwalk and related viruses, and astroviruses).

Examples of fungi include: *Aspergillus* spp., *Blastomyces dermatitidis, Candida albicans*, other *Candida* spp., *Coccidioides immitis, Cryptococcus neoformans, Histoplasma capsulatum, Chlamydia trachomatis, Nocardia* spp., *Pneumocystis carinii*.

Parasites include but are not limited to blood-borne and/or tissues parasites such as *Babesia microti, Babesia divergens,*

*Entamoeba histolytica, Giardia lamblia, Leishmania tropica, Leishmania* spp., *Leishmania braziliensis, Leishmania donovani, Plasmodium falciparum, Plasmodium malariae, Plasmodium ovale, Plasmodium vivax,* and *Toxoplasma gondii, Trypanosoma gambiense* and *Trypanosoma rhodesiense* (African sleeping sickness), *Trypanosoma cruzi* (Chagas' disease), and *Toxoplasma gondii*, flat worms, round worms.

As used herein, "lymph node associated with the target tissue" refers to any lymph node or other lymphoid tissue to which lymph circulating from a tissue is expected or shown to return. As mentioned above, lymphocytes within the blood leave the circulation to sample tissues. In order to return to the circulation, lymphocytes in a tissue make their way through lymphatic endothelium into the lymphatic circulation, flowing to a draining lymph node via afferent lymphatics. The anatomy and association of lymph nodes and the tissues they serve are well known to those of skill in the art. A given target tissue can have more than one draining lymph node. Nonlimiting examples of lymph nodes include aortic, axillary, bronchopulmonary, buccal, celiac, cervical, cystic, deltopectoral, iliac, infraclavicular, inguinal, intercostal, internal thoracic, jugulodigastric, jugulo-omohyoid, lumbar, mastoid, mediastinal, mesenteric, occipital, para-aortic, pararectal, parotid, pectoral, popliteal, preaortic, pulmonary, retroauricular, retropharyngeal, submandibular, submental, subscapular, supratrochlear, tonsils, tracheobroncheal.

Also according to this aspect of the invention, in some embodiments the method further entails administering to the subject an adjuvant. An "adjuvant" as used herein refers to an antigen-nonspecific stimulator of the immune response. The use of adjuvants is essential to induce a strong antibody response to soluble antigens (Harlow and Lane, *Antibodies: A Laboratory Manual*, Cold Spring Harbor, N.Y. Current Edition; hereby incorporated by reference). The overall effect of adjuvants is dramatic and their importance cannot be overemphasized. The action of an adjuvant allows much smaller doses of antigen to be used and generates antibody responses that are more persistent. The nonspecific activation of the immune response often can spell the difference between success and failure in obtaining an immune response. Adjuvants should be used for first injections unless there is some very specific reason to avoid this. Most adjuvants incorporate two components. One component is designed to protect the antigen from rapid catabolism (e.g., liposomes or synthetic surfactants (Hunter et al. 1981)). Liposomes are only effective when the immunogen is incorporated into the outer lipid layer; entrapped molecules are not seen by the immune system. The other component is a substance that will stimulate the immune response nonspecifically. These substances act by raising the level of lymphokines Lymphokines stimulate the activity of antigen-processing cells directly and cause a local inflammatory reaction at the site of injection. Early work relied entirely on heat-killed bacteria (Dienes 1936) or lipopolysaccaride (LPS) (Johnson et al. 1956). LPS is reasonably toxic, and, through analysis of its structural components, most of its properties as an adjuvant have been shown to be in a portion known as lipid A. Lipid A is available in a number of synthetic and natural forms that are much less toxic than LPS but still retain most of the better adjuvant properties of parental LPS molecule. Lipid A compounds are often delivered using liposomes.

Adjuvants include, but are not limited to, alum (e.g., aluminum hydroxide, aluminum phosphate); saponins purified from the bark of the *Q. saponaria* tree, such as QS21 (a glycolipid that elutes in the $21^{st}$ peak with HPLC fractionation; Aquila Biopharmaceuticals, Inc., Worcester, Mass.); poly[di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) andthreonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; Corixa Corporation, Seattle, Wash.), emulsion-based formulations including mineral oil, non-mineral oil, water-in-oil or oil-in-water-in oil emulsion, oil-in-water emulsions such as Seppic ISA series of Montanide adjuvants; and PROVAX, ISCOMs (Immunostimulating complexes which contain mixed saponins, lipids and form virus-sized particles with pores that can hold antigen; SB-AS2 (SmithKline Beecham adjuvant system #2 which is an oil-in-water emulsion containing MPL and QS21: SmithKline Beecham Biologicals [SBB], Rixensart, Belgium); SB-AS4 (SmithKline Beecham adjuvant system #4 which contains alum and MPL; SBB, Belgium); non-ionic block copolymers that form micelles such as CRL 1005 (these contain a linear chain of hydrophobic polyoxypropylene flanked by chains of polyoxyethylene; Vaxcel, Inc., Norcross, Ga.); and Syntex Adjuvant Formulation (SAF, an oil-in-water emulsion containing Tween 80 and a nonionic block copolymer; Syntex Chemicals, Inc., Boulder, Colo.).

In some embodiments the method according to this aspect of the invention further involves administering to the subject an anti-tumor medicament. As used herein, an "anti-tumor medicament" or, equivalently, a "cancer medicament", refers to an agent which is administered to a subject for the purpose of treating a cancer. As used herein, "treating cancer" includes preventing the development of a cancer, reducing the symptoms of cancer, and/or inhibiting the growth of an established cancer. In other aspects, the cancer medicament is administered to a subject at risk of developing a cancer for the purpose of reducing the risk of developing the cancer. Various types of medicaments for the treatment of cancer are described herein. For the purpose of this specification, cancer medicaments are classified as chemotherapeutic agents, immunotherapeutic agents, cancer vaccines, hormone therapy, and biological response modifiers. Additionally, the methods of the invention are intended to embrace the use of more than one cancer medicament along with the TIM-3-binding molecule of the present invention. As an example, where appropriate, the TIM-3-binding molecule can be administered with a both a chemotherapeutic agent and an immunotherapeutic agent. Alternatively, the cancer medicament can embrace an immunotherapeutic agent and a cancer vaccine, or a chemotherapeutic agent and a cancer vaccine, or a chemotherapeutic agent, an immunotherapeutic agent and a cancer vaccine all administered to one subject for the purpose of treating a subject having a cancer or at risk of developing a cancer.

Cancer medicaments function in a variety of ways. Some cancer medicaments work by targeting physiological mechanisms that are specific to tumor cells. Examples include the targeting of specific genes and their gene products (i.e., proteins primarily) which are mutated in cancers. Such genes include but are not limited to oncogenes (e.g., Ras, Her2, bcl-2), tumor suppressor genes (e.g., EGF, p53, Rb), and cell cycle targets (e.g., CDK4, p21, telomerase). Cancer medicaments can alternately target signal transduction pathways and molecular mechanisms which are altered in cancer cells. Targeting of cancer cells via the epitopes expressed on their cell surface is accomplished through the use of monoclonal antibodies. This latter type of cancer medicament is generally referred to herein as immunotherapy.

Other cancer medicaments target cells other than cancer cells. For example, some medicaments prime the immune system to attack tumor cells (i.e., cancer vaccines). Still other medicaments, called angiogenesis inhibitors, function by attacking the blood supply of solid tumors. Since the most malignant cancers are able to metastasize (i.e., exit the primary tumor site and seed a distal tissue, thereby forming a secondary tumor), medicaments that impede this metastasis are also useful in the treatment of cancer. Angiogenesis inhibitors include basic FGF (b-FGF), VEGF, angiopoietins, angiostatin, endostatin, TNF-α, TNP-470, thrombospondin-1, platelet factor 4, CAI, and certain members of the integrin family of proteins. One category of this type of medicament is a metalloproteinase inhibitor, which inhibits the enzymes used by the cancer cells to exist the primary tumor site and extravasate into another tissue.

As used herein, chemotherapeutic agents embrace all other forms of cancer medicaments which do not fall into the categories of immunotherapeutic agents or cancer vaccines. Chemotherapeutic agents as used herein encompass both chemical and biological agents. These agents function to inhibit a cellular activity upon which the cancer cell depends for continued survival. Categories of chemotherapeutic agents include alkylating/alkaloid agents, antimetabolites, hormones or hormone analogs, and miscellaneous antineoplastic drugs. Most if not all of these agents are directly toxic to cancer cells and do not require immune stimulation.

Chemotherapeutic agents which are currently in development or in use in a clinical setting include, without limitation: 5-FU Enhancer, 9-AC, AG2037, AG3340, Aggrecanase Inhibitor, Aminoglutethimide, Amsacrine (m-AMSA), Angiogenesis Inhibitor, Anti-VEGF, Asparaginase, Azacitidine, Batimastat (BB94), BAY 12-9566, BCH-4556, Bis-Naphtalimide, Busulfan, Capecitabine, Carboplatin, Carmustaine+Polifepr Osan, cdk4/cdk2 inhibitors, Chlorombucil, CI-994, Cisplatin, Cladribine, CS-682, Cytarabine HCl, D2163, Dactinomycin, Daunorubicin HCl, DepoCyt, Dexifosamide, Docetaxel, Dolastain, Doxifluridine, Doxorubicin, DX8951f, E 7070, EGFR, Epirubicin, Erythropoietin, Estramustine phosphate sodium, Etoposide (VP16-213), Farnesyl Transferase Inhibitor, FK 317, Flavopiridol, Floxuridine, Fludarabine, Fluorouracil (5-FU), Flutamide, Fragyline, Gemcitabine, Hexamethylmelamine (HMM), Hydroxyurea (hydroxycarbamide), Ifosfamide, Interferon Alfa-2a, Interferon Alfa-2b, Interleukin-2, Irinotecan, ISI 641, Krestin, Lemonal DP 2202, Leuprolide acetate (LHRH-releasing factor analogue), Levamisole, LiGLA (lithium-gamma linolenate), Lodine Seeds, Lometexol, Lomustine (CCNU), Marimistat, Mechlorethamine HCl (nitrogen mustard), Megestrol acetate, Meglamine GLA, Mercaptopurine, Mesna, Mitoguazone (methyl-GAG; methyl glyoxal bis-guanylhydrazone; MGBG), Mitotane (o.p'-DDD), Mitoxantrone, Mitoxantrone HCl, MMI 270, MMP, MTA/LY 231514, Octreotide, ODN 698, OK-432, Oral Platinum, Oral Taxoid, Paclitaxel (TAXOL®), PARP Inhibitors, PD 183805, Pentostatin (2' deoxycoformycin), PKC 412, Plicamycin, Procarbazine HCl, PSC 833, Ralitrexed, RAS Farnesyl Transferase Inhibitor, RAS Oncogene Inhibitor, Semustine (methyl-CCNU), Streptozocin, Suramin, Tamoxifen citrate, Taxane Analog, Temozolomide, Teniposide (VM-26), Thioguanine, Thiotepa, Topotecan, Tyrosine Kinase, UFT (Tegafur/Uracil), Valrubicin, VEGF/ b-FGF Inhibitors, Vinblastine sulfate, Vindesine sulfate, VX-710, VX-853, YM 116, ZD 0101, ZD 0473/Anormed, ZD 1839, ZD 9331.

Immunotherapeutic agents are medicaments which derive from antibodies or antibody fragments which specifically bind or recognize a cancer antigen. The goal of immunotherapy is to augment a patient's immune response to an established tumor. One method of immunotherapy includes the use of adjuvants. Adjuvant substances derived from microorganisms, such as *bacillus* Calmette-Guérin, heighten the immune response and enhance resistance to tumors in animals.

Some cancer cells are antigenic and thus can be targeted by the immune system. In one aspect, the combined administration of TIM-3-binding molecule and cancer medicaments, particularly those which are classified as cancer immunotherapies, is useful for stimulating a specific immune response against a tumor antigen.

As used herein, the terms "tumor antigen" and "cancer antigen" are used interchangeably to refer to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses.

A tumor antigen is typically a peptide associated with the surface of a tumor or cancer cell and which is capable of provoking an immune response when expressed on the surface of an APC in the context of an MHC molecule. Cancer antigens, such as those present in cancer vaccines or those used to prepare cancer immunotherapies, can be prepared from crude cancer cell extracts, as described in Cohen P A et al. (1994) *Cancer Res* 54:1055-8, or by partially purifying the antigens, using recombinant technology, or de novo synthesis of known antigens. Cancer antigens can be used in the form of immunogenic portions of a particular antigen or in some instances a whole cell or a tumor mass can be used as the antigen. Such antigens can be isolated or prepared recombinantly or by any other means known in the art.

The theory of immune surveillance is that a prime function of the immune system is to detect and eliminate neoplastic cells before a tumor forms. A basic principle of this theory is that cancer cells are antigenically different from normal cells and thus elicit immune reactions that are similar to those that cause rejection of immunologically incompatible allografts. Studies have confirmed that tumor cells differ, either qualitatively or quantitatively, in their expression of antigens. For example, "tumor-specific antigens" are antigens that are specifically associated with tumor cells but not normal cells. Examples of tumor-specific antigens are viral antigens in tumors induced by DNA or RNA viruses. "Tumor-associated" antigens are present in both tumor cells and normal cells but are present in a different quantity or a different form in tumor cells. Examples of such antigens are oncofetal antigens (e.g., carcinoembryonic antigen), differentiation antigens (e.g., T and Tn antigens), and oncogene products (e.g., HER/neu).

As previously noted, the polypeptide products of tumor-specific genes can be the targets for host immune surveillance and provoke selection and expansion of one or more clones of CTLs specific for the tumor-specific gene product. Examples of this phenomenon include proteins and fragments thereof encoded by the MAGE family of genes. In PCT application PCT/US92/04354, published on Nov. 26, 1992, the "MAGE" family, a tumor-specific family of genes, is disclosed. The expression products of these genes are processed into peptides which, in turn, are expressed on cell surfaces. This can lead to lysis of the tumor cells by specific CTLs. The genes are said to code for "tumor rejection antigen precursors" or "TRAP" molecules, and the peptides derived therefrom are referred to as "tumor rejection antigens" or "TRAs". See Traversari C et al. (1992) *Immunogenetics* 35:145-52; van der Bruggen P et al. (1991) *Science* 254:1643-47, for further information on this family of genes. Also, see U.S. Pat. No. 5,342,774.

In addition to the MAGE family of genes, tumor antigens are also encoded by the MAGE-Xp family of genes (U.S. Pat. No. 5,587,289), the tyrosinase gene (PCT publication WO94/14459), the Melan-A gene (PCT publication WO94/21126), the BAGE gene (U.S. Pat. No. 5,571,711 and PCT publication WO95/00159), the GAGE gene (U.S. Pat. No. 5,610,013 and PCT publication WO95/03422), the RAGE family of genes (U.S. Pat. No. 5,939,526), the PRAME (formerly DAGE) gene (PCT publication WO96/10577), the MUM-1/LB-33B gene (U.S. Pat. No. 5,589,334), the NAG gene (U.S. Pat. No. 5,821,122), the FB5 (endosialin) gene (U.S. Pat. No. 6,217,868), and the PMSA gene (U.S. Pat. No. 5,939,818). The foregoing list is only intended to be representative and is not to be understood to be limiting.

Different types of cells that can kill tumor targets in vitro and in vivo have been identified: natural killer cells (NK cells), cytotoxic T lymphocytes (CTLs), lymphokine-activated killer cells (LAKs), and activated macrophages. NK cells can kill tumor cells without having been previously sensitized to specific antigens, and the activity does not require the presence of class I antigens encoded by the major histocompatibility complex (MHC) on target cells. NK cells are thought to participate in the control of nascent tumors and in the control of metastatic growth. In contrast to NK cells, CTLs can kill tumor cells only after they have been sensitized to tumor antigens and when the target antigen is expressed on the tumor cells that also express MHC class I. CTLs are thought to be effector cells in the rejection of transplanted tumors and of tumors caused by DNA viruses. LAK cells are a subset of null lymphocytes distinct from the NK cell and CTL populations. Activated macrophages can kill tumor cells in a manner that is not antigen-dependent nor MHC-restricted once activated. Activated macrophages are thought to decrease the growth rate of the tumors they infiltrate. In vitro assays have identified other immune mechanisms such as antibody-dependent, cell-mediated cytotoxic reactions and lysis by antibody plus complement. However, these immune effector mechanisms are thought to be less important in vivo than the function of NK cells, CTLs, LAK cells, and macrophages in vivo (for review see Piessens W F and David J, "Tumor Immunology", In: *Scientific American Medicine*, Vol. 2, Scientific American Books, N.Y., pp. 1-13, 1996).

In some embodiments the anti-tumor medicament includes a tumor-specific antibody or tumor-specific fragment thereof. The term "tumor-specific antibody" refers to an antibody that specifically binds to a tumor antigen. A "tumor-specific antibody fragment" as used herein refers to a fragment of a tumor-specific antibody that binds specifically to a tumor antigen. Typically the fragment includes at least part of a variable domain including a hypervariable region that contributes to antigen specificity and binding. Examples of tumor-specific antibody fragments include, without limitation, Fab, Fv, Fab', and F(ab')$_2$ fragments derived from tumor-specific antibodies.

Preferably, the tumor antigen is expressed at the cell surface of the cancer cell. Even more preferably, the antigen is one which is not expressed by normal cells, or at least not expressed to the same level as in cancer cells. Antibody-based immunotherapies may function by binding to the cell surface of a cancer cell and thereby stimulate the endogenous immune system to attack the cancer cell. Another way in which antibody-based therapy functions is as a delivery system for the specific targeting of toxic substances to cancer cells. Antibodies are usually conjugated to toxins such as ricin (e.g., from castor beans), calicheamicin and maytansinoids, to radioactive isotopes such as Iodine-131 and Yttrium-90, to chemotherapeutic agents (as described herein), or to biological response modifiers. In this way, the toxic substances can be concentrated in the region of the cancer and non-specific toxicity to normal cells can be minimized.

In addition to the use of antibodies which are specific for cancer antigens, antibodies which bind to vasculature, such as those which bind to endothelial cells, are also useful in the invention. Solid tumors generally are dependent upon newly formed blood vessels to survive, and thus most tumors are capable of recruiting and stimulating the growth of new blood vessels. As a result, one strategy of many cancer medicaments is to attack the blood vessels feeding a tumor and/or the connective tissues (or stroma) supporting such blood vessels.

Examples of cancer immunotherapies which are currently being used or which are in development include but are not limited to Rituxan, IDEC-C2B8, anti-CD20 Mab, Panorex, 3622W94, anti-EGP40 (17-1A) pancarcinoma antigen on adenocarcinomas Herceptin, anti-Her2, Anti-EGFr, BEC2, anti-idiotypic-GD$_3$ epitope, Ovarex, B43.13, anti-idiotypic CA125, 4B5, Anti-VEGF, RhuMAb, MDX-210, anti-HER-2, MDX-22, MDX-220, MDX-447, MDX-260, anti-GD-2, Quadramet, CYT-424, IDEC-Y2B8, Oncolym, Lym-1, SMART M195, ATRAGEN, LDP-03, anti-CAMPATH, ior t6, anti CD6, MDX-11, OV103, Zenapax, Anti-Tac, anti-IL-2 receptor, MELIMMUNE-2, MELIMMUNE-1, CEACIDE, Pretarget, NovoMAb-G2, TNT, anti-histone, Gliomab-H, GNI-250, EMD-72000, LymphoCide, CMA 676, Monopharm-C, ior egf/r3, ior c5, anti-FLK-2, SMART 1D10, SMART ABL 364, and ImmuRAIT-CEA.

Cancer vaccines are medicaments which are intended to stimulate an endogenous immune response against cancer cells. Currently produced vaccines predominantly activate the humoral immune system (i.e., the antibody dependent immune response). Other vaccines currently in development are focused on activating the cell-mediated immune system including cytotoxic T lymphocytes which are capable of killing tumor cells. Cancer vaccines generally enhance the presentation of cancer antigens to both APCs (e.g., macrophages and dendritic cells) and/or to other immune cells such as T cells, B cells, and NK cells.

Although cancer vaccines can take one of several forms, as discussed infra, their purpose is to deliver cancer antigens and/or cancer associated antigens to APCs in order to facilitate the endogenous processing of such antigens by APC and the ultimate presentation of antigen presentation on the cell surface in the context of MHC class I molecules. One form of cancer vaccine is a whole cell vaccine which is a preparation of cancer cells which have been removed from a subject, treated ex vivo and then reintroduced as whole cells in the subject. Lysates of tumor cells can also be used as cancer vaccines to elicit an immune response. Another form of cancer vaccine is a peptide vaccine which uses cancer-specific or cancer-associated small proteins to activate T cells. Cancer-associated proteins are proteins which are not exclusively expressed by cancer cells (i.e., other normal cells can still express these antigens). However, the expression of cancer-associated antigens is generally consistently upregulated with cancers of a particular type. Yet another form of cancer vaccine is a dendritic cell vaccine which includes whole dendritic cells which have been exposed to a cancer antigen or a cancer-associated antigen in vitro. Lysates or membrane fractions of dendritic cells can also be used as cancer vaccines. Dendritic cell vaccines are able to activate APCs directly. Other cancer vaccines include ganglioside vaccines, heat-shock protein vaccines, viral and bacterial vaccines, and nucleic acid vaccines.

In some embodiments the method also includes administering to the subject a cytokine A "cytokine" as used herein refers to any of a diverse group of soluble proteins and peptides which act as humoral regulators at nano- to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to interleukins IL-1, IL-2, IL-4, IL-5, IL-6, IL-7, IL-10, IL-12, IL-15, IL-18; granulocyte-macrophage colony-stimulating factor (GM-CSF); granulocyte colony-stimulating factor (G-CSF); interferons including interferon-alpha (IFN-α), interferon-beta (IFN-β), and interferon-gamma (IFN-γ); tumor necrosis factor (TNF), transforming growth factor-beta (TGF-β); FLT-3 ligand; and CD40 ligand.

Cytokines play a role in directing the T cell response. Helper (CD4+) T cells orchestrate the immune response of mammals through production of soluble factors that act on other immune system cells, including other T cells. Most mature CD4+ T helper cells express one of two cytokine profiles: Th1 or Th2. The Th1 subset in mice promotes delayed-type hypersensitivity, cell-mediated immunity, and immunoglobulin class switching to IgG2a. The Th2 subset in mice induces humoral immunity by activating B cells, promoting antibody production, and inducing class switching to IgG1 and IgE. In some embodiments, it is preferred that the cytokine be a Th1 cytokine.

In some embodiments the method according to this aspect of the invention further involves administering to the subject an antibacterial medicament. An "antibacterial medicament" refers to an agent that kills or inhibits the growth or function of bacteria. Antibacterial agents which are effective for killing or inhibiting a wide range of bacteria are often referred to as broad spectrum antibiotics. Other types of antibacterial agents are predominantly effective against Gram-positive bacteria or Gram-negative bacteria. These types of antibacterial agents are frequently referred to as narrow spectrum antibiotics. Other antibacterial agents which are effective against a single organism or disease and not against other types of bacteria, are often referred to as limited spectrum antibiotics. Antibacterial agents are sometimes classified based on their primary mode of action. In general, antibacterial agents are cell wall synthesis inhibitors, cell membrane inhibitors, protein synthesis inhibitors, nucleic acid synthesis or functional inhibitors, and competitive inhibitors.

Antibacterial agents useful in the invention include but are not limited to natural penicillins, semi-synthetic penicillins, clavulanic acid, cephalolsporins, bacitracin, ampicillin, carbenicillin, oxacillin, azlocillin, mezlocillin, piperacillin, methicillin, dicloxacillin, nafcillin, cephalothin, cephapirin, cephalexin, cefamandole, cefaclor, cefazolin, cefuroxine, cefoxitin, cefotaxime, cefsulodin, cefetamet, cefixime, ceftriaxone, cefoperazone, ceftazidine, moxalactam, carbapenems, imipenems, monobactems, eurtreonam, vancomycin, polymyxin, amphotericin B, nystatin, imidazoles, clotrimazole, miconazole, ketoconazole, itraconazole, fluconazole, rifampins, ethambutol, tetracyclines, chloramphenicol, macrolides, aminoglycosides, streptomycin, kanamycin, tobramycin, amikacin, gentamicin, tetracycline, minocycline, doxycycline, chlortetracycline, erythromycin, roxithromycin, clarithromycin, oleandomycin, azithromycin, chloramphenicol, quinolones, co-trimoxazole, norfloxacin, ciprofloxacin, enoxacin, nalidixic acid, temafloxacin, sulfonamides, gantrisin, and trimethoprim; Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefinenoxime Hydrochloride; Cefinetazole; Cefinetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; and Zorbamycin.

In some embodiments the method further involves administering to the subject an antiviral medicament. As used herein, an "antiviral medicament" refers to a compound which prevents infection of cells by viruses or replication of the virus within the cell. There are many fewer antiviral drugs than antibacterial drugs because the process of viral replication is so closely related to DNA replication within the host cell, that non-specific antiviral agents would often be toxic to the host. There are several stages within the process of viral infection which can be blocked or inhibited by antiviral agents. These stages include, attachment of the virus to the host cell (immunoglobulin or binding peptides), uncoating of the virus (e.g., amantadine), synthesis or translation of viral mRNA (e.g., interferon), replication of viral RNA or DNA (e.g., nucleoside analogues), maturation of new virus proteins (e.g., protease inhibitors), and budding and release of the virus.

Nucleotide analogues are synthetic compounds which are similar to nucleotides, but which have an incomplete or abnormal deoxyribose or ribose group. Once the nucleotide analogues are in the cell, they are phosphorylated, producing the triphosphate formed which competes with normal nucleotides for incorporation into the viral DNA or RNA. Once the triphosphate form of the nucleotide analogue is incorporated into the growing nucleic acid chain, it causes irreversible association with the viral polymerase and thus chain termination. Nucleotide analogues include, but are not limited to, acyclovir (used for the treatment of herpes simplex virus and varicella-zoster virus), gancyclovir (useful for the treatment of cytomegalovirus), idoxuridine, ribavirin (useful for the treatment of respiratory syncitial virus), dideoxyinosine, dideoxycytidine, and zidovudine (azidothymidine).

The interferons are cytokines which are secreted by virus-infected cells as well as immune cells. The interferons function by binding to specific receptors on cells adjacent to the infected cells, causing the change in the cell which protects it from infection by the virus. IFN-α and IFN-β also induce the expression of Class I and Class II MHC molecules on the surface of infected cells, resulting in increased antigen presentation for host immune cell recognition. These interferons are available as recombinant forms and have been used for the treatment of chronic hepatitis B and C infection. At the dosages which are effective for antiviral therapy, interferons sometimes have severe side effects such as fever, malaise and weight loss.

Immunoglobulin therapy is used for the prevention of viral infection. Immunoglobulin therapy for viral infections is different than bacterial infections, because rather than being antigen-specific, the immunoglobulin therapy functions by binding to extracellular virions and preventing them from attaching to and entering cells which are susceptible to the viral infection. The therapy is useful for the prevention of viral infection for the period of time that the antibodies are present in the host. In general there are two types of immunoglobulin therapies, normal immune globulin therapy and hyper-immune globulin therapy. Normal immune globulin therapy utilizes an antibody product which is prepared from the serum of normal blood donors and pooled. This pooled product contains low titers of antibody to a wide range of human viruses, such as hepatitis A, parvovirus, enterovirus (especially in neonates). Hyper-immune globulin therapy utilizes antibodies which are prepared from the serum of individuals who have high titers of an antibody to a particular virus. Those antibodies are then used against a specific virus. Examples of hyper-immune globulins include zoster immune globulin (useful for the prevention of varicella in immuno-compromised children and neonates), human rabies immunoglobulin (useful in the post-exposure prophylaxis of a subject bitten by a rabid animal), hepatitis B immune globulin (useful in the prevention of hepatitis B virus, especially in a subject exposed to the virus), and RSV immune globulin (useful in the treatment of respiratory syncitial virus infections).

Thus, antiviral medicaments useful in the invention include but are not limited to immunoglobulins, amantadine, interferon, nucleoside analogues, and protease inhibitors. Specific examples of antiviral agents include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime.

In some embodiments the method according to this aspect of the invention further involves administering to the subject an antifungal medicament. An "antifungal medicament" is an agent that kills or inhibits the growth or function of infective fungi. Anti-fungal medicaments are sometimes classified by their mechanism of action. Some anti-fungal agents function as cell wall inhibitors by inhibiting glucose synthase. These include, but are not limited to, basiungin/ECB. Other antifungal agents function by destabilizing membrane integrity. These include, but are not limited to, imidazoles, such as clotrimazole, sertaconzole, fluconazole, itraconazole, ketoconazole, miconazole, and voriconacole, as well as FK 463, amphotericin B, BAY 38-9502, MK 991, pradimicin, UK 292, butenafine, and terbinafine. Other antifungal agents function by breaking down chitin (e.g., chitinase) or immunosuppression (501 cream).

Thus, the antifungal medicaments useful in the invention include but are not limited to imidazoles, 501 cream, and Acrisorcin, Ambruticin, Amorolfine, Amphotericin B, Azaconazole, Azaserine, Basifungin, BAY 38-9502, Bifonazole, Biphenamine Hydrochloride, Bispyrithione Magsulfex, Butenafine, Butoconazole Nitrate, Calcium Undecylenate, Candicidin, Carbol-Fuchsin, Chitinase, Chlordantoin, Ciclopirox, Ciclopirox Olamine, Cilofungin, Cisconazole, Clotrimazole, Cuprimyxin, Denofungin, Dipyrithione, Doconazole, Econazole, Econazole Nitrate, Enilconazole, Ethonam Nitrate, Fenticonazole Nitrate, Filipin, FK 463, Fluconazole, Flucytosine, Fungimycin, Griseofulvin, Hamycin, Isoconazole, Itraconazole, Kalafungin, Ketoconazole, Lomofungin, Lydimycin, Mepartricin, Miconazole, Miconazole Nitrate, MK 991, Monensin, Monensin Sodium, Naftifine Hydrochloride, Neomycin Undecylenate, Nifuratel, Nifurmerone, Nitralamine Hydrochloride, Nystatin, Octanoic Acid, Orconazole Nitrate, Oxiconazole Nitrate, Oxifungin Hydrochloride, Parconazole Hydrochloride, Partricin, Potassium Iodide, Pradimicin, Proclonol, Pyrithione Zinc, PyrroInitrin, Rutamycin, Sanguinarium Chloride, Saperconazole, Scopafungin, Selenium Sulfide, Sertaconazole, Sinefungin, Sulconazole Nitrate, Terbinafine, Terconazole, Thiram, Ticlatone, Tioconazole, Tolciclate, Tolindate, Tolnaftate, Triacetin, Triafungin, UK 292, Undecylenic Acid, Viridofulvin, Voriconazole, Zinc Undecylenate, and Zinoconazole Hydrochloride.

In some embodiments the method further involves administering to the subject an antiparasitic medicament. An "antiparasitic medicament" refers to an agent that kills or inhibits the growth or function of infective parasites. Examples of antiparasitic medicaments, also referred to as parasiticides, useful in the invention include but are not limited to albendazole, amphotericin B, benznidazole, bithionol, chloroquine HCl, chloroquine phosphate, clindamycin, dehydroemetine, diethylcarbamazine, diloxanide furoate, doxycycline, eflornithine, furazolidaone, glucocorticoids, halofantrine, iodoquinol, ivermectin, mebendazole, mefloquine, meglumine antimoniate, melarsoprol, metrifonate, metronidazole, niclosamide, nifurtimox, oxamniquine, paromomycin, pentamidine isethionate, piperazine, praziquantel, primaquine phosphate, proguanil, pyrantel pamoate, pyrimethanmine-sulfonamides, pyrimethanmine-sulfadoxine, quinacrine HCl, quinine sulfate, quinidine gluconate, spiramycin, stibogluconate sodium (sodium antimony gluconate), suramin, tetracycline, thiabendazole, timidazole, trimethroprim-sulfamethoxazole, and tryparsamide, some of which are used alone or in combination with others.

Certain aspects of the invention involve methods which inhibit T-cell trafficking into selected tissues.

Accordingly, in another aspect the invention provides a method for reducing T-cell trafficking into a target tissue of a subject. The method according to this aspect involves administering to the subject a TIM-3 ligand-binding molecule in an effective amount to reduce T-cell trafficking to a target tissue of the subject. A "TIM-3 ligand-binding molecule" as used herein refers to any molecule, including TIM-3, that binds to TIM-3 ligand.

In addition to TIM-3 itself, the TIM-3 ligand-binding molecule can be a small molecule, a polypeptide, an antibody or a fragment of an antibody, a polynucleotide, a carbohydrate including a polysaccharide, a lipid, a drug, as well as mimics, derivatives, and combinations thereof. The TIM-3 ligand-binding molecule can be found in nature or it can be derived or synthesized using suitable in vitro and synthetic methods known by those of skill in the art. For example, the TIM-3 ligand-binding molecule can be a small molecule that is identified through screening a library of small molecules for the ability to bind to TIM-3 ligand. As another example, the TIM-3 ligand-binding molecule can be generated and identified using phage display of peptides.

In some embodiments the TIM-3 ligand-binding molecule is a soluble TIM-3. "Soluble TIM-3" refers to any form of TIM-3, including functional variants of TIM-3, that is dissociated from cell membrane. Soluble TIM-3 can be a C-terminal truncated form of full-length TIM-3 or a transmembrane-deleted version of TIM-3. In some embodiments the TIM-3 ligand-binding molecule includes a single domain of the extracellular region of TIM-3, i.e., the IgV domain or the mucin domain. In one embodiment the soluble TIM-3 is an alternatively spliced variant of full-length TIM-3, which includes the IgV domain and intracellular region but not the mucin domain or transmembrane region. In some embodiments the TIM-3 ligand-binding molecule includes an extracellular region of TIM-3.

In some embodiments the soluble TIM-3 is a fusion protein including at least one domain of an extracellular region of TIM-3 and a constant heavy chain or portion thereof of an immunoglobulin. In one embodiment soluble TIM-3 refers to a fusion protein that includes at least one domain of an extracellular domain of TIM-3 and another polypeptide. In one embodiment the soluble TIM-3 is a fusion protein including the extracellular region of TIM-3 covalently linked, e.g., via a peptide bond, to an Fc fragment of an immunoglobulin such as IgG; such a fusion protein typically is a homodimer. In one embodiment the soluble TIM-3 is a fusion protein including just the IgV domain of the extracellular region of TIM-3 covalently linked, e.g., via a peptide bond, to an Fc fragment of an immunoglobulin such as IgG; such a fusion protein typically is a homodimer. As is well known in the art, an Fc fragment is a homodimer of two partial constant heavy chains. Each constant heavy chain includes at least a CH1 domain, the hinge, and CH2 and CH3 domains. Each monomer of such an Fc fusion protein includes an extracellular region of TIM-3 linked to a constant heavy chain or portion thereof (e.g., hinge, CH2, CH3 domains) of an immunoglobulin. The constant heavy chain in some embodiments will include part or all of the CH1 domain that is N-terminal to the hinge region of immunoglobulin. In other embodiments the constant heavy chain will include the hinge but not the CH1 domain. In yet other embodiments the constant heavy chain will exclude the hinge and the CH1 domain, e.g., it will include only the CH2 and CH3 domains of IgG.

In some embodiments the subject is in need of treatment for an autoimmune disease of the target tissue. "Autoimmune disease" is a class of diseases in which a subject's own antibodies react with host tissue or in which immune effector T cells are autoreactive to endogenous self-peptides and cause destruction of tissue. Thus an immune response is mounted against a subject's own antigens, referred to as self-antigens. Autoimmune diseases include but are not limited to rheumatoid arthritis, Crohn's disease, multiple sclerosis, systemic lupus erythematosus (SLE), autoimmune encephalomyelitis, myasthenia gravis (MG), Hashimoto's thyroiditis, Goodpasture's syndrome, pemphigus (e.g., pemphigus vulgaris), Grave's disease, autoimmune hemolytic anemia, autoimmune thrombocytopenic purpura, scleroderma with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, Sjögren's syndrome, insulin resistance, and autoimmune diabetes mellitus (type 1 diabetes mellitus; insulin-dependent diabetes mellitus). Recently autoimmune disease has been recognized also to encompass atherosclerosis and Alzheimer's disease.

A "self-antigen" as used herein refers to an antigen of a normal host tissue. Normal host tissue does not include cancer cells. Thus an immune response mounted against a self-antigen, in the context of an autoimmune disease, is an undesirable immune response and contributes to destruction and damage of normal tissue, whereas an immune response mounted against a cancer antigen is a desirable immune response and contributes to destruction of the tumor or cancer.

In yet another aspect the invention provides a method for treating or preventing asthma or allergy. The method according to this aspect of the invention involves increasing activity or expression of TIM-3 in a T cell of a subject to treat or prevent asthma or allergy.

As used herein, "asthma" shall refer to a disorder of the respiratory system characterized by inflammation and narrowing of the airways and increased reactivity of the airways to inhaled agents. Asthma is frequently, although not exclusively, associated with atopic or allergic symptoms.

As used herein, "allergy" shall refer to acquired hypersensitivity to a substance (allergen). Allergic conditions include eczema, allergic rhinitis or coryza, hay fever, bronchial asthma, urticaria (hives) and food allergies, and other atopic conditions. A "subject having an allergy" is a subject that has or is at risk of developing an allergic reaction in response to an allergen. An "allergen" refers to a substance that can induce an allergic or asthmatic response in a susceptible subject. The list of allergens is enormous and can include pollens, insect venoms, animal dander, dust, fungal spores and drugs (e.g., penicillin).

Examples of natural animal and plant allergens include proteins specific to the following genuses: *Canine* (*Canis familiaris*); *Dermatophagoides* (e.g., *Dermatophagoides farinae*); *Felis* (*Felis domesticus*); *Ambrosia* (*Ambrosia artemiisfolia; Lolium* (e.g., *Lolium perenne* or *Lolium multiflorum*); *Cryptomeria* (*Cryptomeria japonica*); *Alternaria* (*Alternaria alternate*); *Alder; Alnus* (*Alnus gultinosa*); *Betula* (*Betula verrucosa*); *Quercus* (*Quercus alba*); *Olea* (*Olea europa*); *Artemisia* (*Artemisia vulgaris*); *Plantago* (e.g., *Plantago lanceolata*); *Parietaria* (e.g., *Parietaria officinalis* or *Parietaria judaica*); *Blattella* (e.g., *Blattella germanica*); *Apis* (e.g., *Apis multiflorum*); *Cupressus* (e.g., *Cupressus sempervirens, Cupressus arizonica* and *Cupressus macrocarpa*); *Juniperus* (e.g., *Juniperus sabinoides, Juniperus virginiana, Juniperus communis* and *Juniperus ashei*); *Thuya* (e.g., *Thuya orientalis*); *Chamaecyparis* (e.g., *Chamaecyparis obtusa*); *Periplaneta* (e.g., *Periplaneta americana*); *Agropyron* (e.g., *Agropyron repens*); *Secale* (e.g., *Secale cereale*); *Triticum* (e.g., *Triticum aestivum*); *Dactylis* (e.g., *Dactylis glomerate*); *Festuca* (e.g., *Festuca elation*); *Poa* (e.g., *Poa pratensis* or *Poa compressa*); *Avena* (e.g., *Avena sativa*); *Holcus* (e.g., *Holcus lanatus*); *Anthoxanthum* (e.g., *Anthoxanthum odoratum*); *Arrhenatherum* (e.g., *Arrhenatherum elatius*); *Agrostis* (e.g., *Agrostis alba*); *Phleum* (e.g., *Phleum pratense*); *Phalaris* (e.g., *Phalaris arundinacea*); *Paspalum* (e.g., *Paspalum notatum*); *Sorghum* (e.g., *Sorghum halepensis*); and *Bromus* (e.g., *Bromus inermis*).

According to a further aspect, the invention provides a method for treating a Th2-mediated disorder in a subject The method involves expressing TIM-3 on the surface of Th2 cells of a subject having a Th2-mediated disorder in an amount effective to treat the Th2-mediated disorder. A "Th2-mediated disorder" as used herein refers to a disease that is associated with the development of a Th2 immune response. A "Th2 immune response" as used herein refers to the induction of at least one Th2-cytokine or a Th2-antibody. In preferred embodiments more than one Th2-cytokine or Th2-antibody is induced. Thus a Th2-mediated disease is a disease associated with the induction of a Th2 response and refers to the partial or complete induction of at least one Th2-cytokine or Th2-antibody or an increase in the levels of at least one Th2-cytokine or Th2-antibody. These disorders are known in the art and include for instance, but are not limited to, atopic conditions, such as asthma and allergy, including allergic rhinitis, gastrointestinal allergies, including food allergies, eosinophilia, conjunctivitis, glomerulonephritis, certain pathogen susceptibilities such as helminthic (e.g., leishmaniasis) and certain viral infections, including human immunodeficiency virus (HIV), and certain bacterial infections, including tuberculosis and lepromatous leprosy.

In contrast to a Th2-mediated disorder, a "Th1-mediated disorder" as used herein refers to a disease that is associated with the development of a Th1 immune response. A "Th1 immune response" as used herein refers to the induction of at least one Th1-cytokine or a Th1-antibody. In preferred embodiments more than one Th1-cytokine or Th1-antibody is induced. Thus a Th1-mediated disease is a disease associated with the induction of a Th1 response and refers to the partial or complete induction of at least one Th1-cytokine or Th1-antibody or an increase in the levels of at least one Th1-cytokine or Th1-antibody. These disorders are known in the art and include for instance, but are not limited to, autoimmune (especially organ-specific) disease, psoriasis, Th1 inflammatory disorders, infection with extracellular parasites (e.g., response to helminths), solid organ allograft rejection (e.g., acute kidney allograft rejection), symptoms associated with hepatitis B (HBV) infection (e.g., HBV acute phase or recovery phase), chronic hepatitis C(HCV) infection, insulin-dependent diabetes mellitus (IDDM), multiple sclerosis (MS), subacute lymphocytic thyroiditis ("silent thyroiditis"), Crohn's disease, primary biliary cirrhosis, primary sclerosing cholangitis, sarcoidosis, atherosclerosis, acute graft-versus-host disease (GvHD), glomerulonephritis, anti-glomerular basement membrane disease, Wegener's granulomatosis, inflammatory myopathies, Sjögren's syndrome, Behçet's syndrome, rheumatoid arthritis, Lyme arthritis, and unexplained recurrent abortion. In some embodiments the Th1-mediated disorder is selected from the group consisting of atherosclerosis, infection with extracellular parasites, symptoms associated with hepatitis B (HBV) infection (e.g., HBV acute phase or recovery phase), chronic hepatitis C(HCV) infection, silent thyroiditis, primary biliary cirrhosis, primary sclerosing cholangitis, glomerulonephritis, anti-glomerular basement membrane disease, Wegener's granulomatosis, inflammatory myopathies, Sjögren's syndrome, Behçet's syndrome, rheumatoid arthritis, and unexplained recurrent abortion.

According to another aspect, the invention provides a method for promoting APC activation. The method according to this aspect involves contacting a T cell with a TIM-3-binding molecule, and contacting an APC with the T cell to activate the APC.

An "antigen-presenting cell" or, equivalently, an "APC" as used herein refers to a specialized cell, either belonging to the immune system or capable of interacting with a cell belonging to the immune system, that presents on its cell surface a complex between an antigen and a major histocompatibility complex (MHC) molecule. In addition to presenting antigen in the context of self (i.e., self-MHC) to antigen-specific lymphocytes, APCs frequently also provide additional costimulatory signals to lymphocytes so engaged, through cognate interactions between additional cell surface receptor/counter-receptor pairs and through secreted products, e.g., cytokines and chemokines APCs are believed to include mononuclear phagocytes (e.g., monocyte/macrophages), B lymphocytes, dendritic cells, Langerhans cells, and certain endothelial cells. In certain embodiments an APC is a macrophage. In certain embodiments an APC is a dendritic cell. It has been discovered according to the present invention, for example, that certain APCs, including macrophages and dendritic cells, express TIM-3 ligand on their cell surface.

According to yet another aspect of the invention, a method is provided for inhibiting APC activation. The method involves contacting an APC with an effective amount of an agent that reduces activity or expression of TIM-3 to inhibit activation of the APC. An "agent that reduces activity or expression of TIM-3" as used herein refers to an agent that reduces the function of TIM-3 either by effectively blocking interaction of TIM-3 with its ligand or by interfering with expression of TIM-3. Such agents can take the form of TIM-3-binding molecules, TIM-3 ligand-binding molecules, and antisense to TIM-3.

According to another aspect the invention further provides a method for treating or preventing intracellular infections. The method according to this aspect involves promoting macrophage activation by contacting a TIM-3 ligand on the macrophage with a TIM-3 expressing cell. An "intracellular infection" as used herein refers to an infection by an infectious organism or agent wherein the infectious organism or agent survives and replicates within a cell of the infected host. A number of bacteria, fungi, parasites, and all viruses are involved in intracellular infections. Intracellular bacteria such as *Listeria monocytogenes* and various mycobacteria, including *M. tuberculosis*, are resistant to degradation within macrophages and are therefore capable of surviving and replicating within phagocytes. Such intracellular bacteria normally pose a special challenge to the immune system's ability to eradicate the infecting organisms. Another important example of an intracellular infection is that involving the obligate intracellular protozoa of the genus *Leishmania*.

When administered to a subject, the TIM-3-binding molecule and TIM-3 ligand-binding molecule of the present invention are administered in pharmaceutically acceptable preparations. Such preparations may routinely contain pharmaceutically acceptable concentrations of salt, buffering agents, preservatives, compatible carriers, supplementary agents such as adjuvants and cytokines, and optionally other therapeutic agents. Thus, "cocktails" including the TIM-3-binding molecule and TIM-3 ligand-binding molecule and optional supplementary agents are contemplated. The supplementary agents themselves can be conjugated to TIM-3-binding molecule or TIM-3 ligand-binding molecule to enhance delivery of the supplementary agents.

The preferred amount of TIM-3-binding molecule or TIM-3 ligand-binding molecule in all pharmaceutical preparations made in accordance with the present invention should be a therapeutically effective amount thereof which is also a medically acceptable amount thereof. Actual dosage levels of TIM-3-binding molecule or TIM-3 ligand-binding molecule in the pharmaceutical compositions of the present invention can be varied so as to obtain an amount of TIM-3-binding molecule or TIM-3 ligand-binding molecule which is effective to achieve the desired therapeutic response for a particular patient, pharmaceutical composition of TIM-3-binding molecule or TIM-3 ligand-binding molecule, and mode of administration, without being toxic to the patient.

The selected dosage level and frequency of administration will depend upon a variety of factors including the route of administration, the time of administration, the rate of excretion of the therapeutic agent(s) including TIM-3-binding molecule and TIM-3 ligand-binding molecule, the duration of the treatment, other drugs, compounds and/or materials used in combination with TIM-3-binding molecule or TIM-3 ligand-binding molecule, the age, sex, weight, condition, general health and prior medical history of the patient being treated and the like factors well known in the medical arts. For example, the dosage regimen is likely to vary with pregnant women, nursing mothers and children relative to healthy adults.

A physician having ordinary skill in the art can readily determine and prescribe the therapeutically effective amount of the pharmaceutical composition required. For example, the physician could start doses of TIM-3-binding molecule or TIM-3 ligand-binding molecule employed in the pharmaceutical composition of the present invention at levels lower than that required to achieve the desired therapeutic effect and gradually increase the dosage until the desired effect is achieved.

For use in therapy, the TIM-3-binding molecule and TIM-3 ligand-binding molecule can be formulated as pharmaceutical compositions. The pharmaceutical compositions of the invention contain an effective amount of TIM-3-binding molecule or TIM-3 ligand-binding molecule, and optionally another medicament, in a pharmaceutically acceptable carrier. The term "pharmaceutically acceptable carrier" means one or more compatible solid or liquid fillers, diluants or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the TIM-3-binding molecule or TIM-3 ligand-binding molecule of the present invention, and with each other, in a manner such that there is no interaction which would substantially impair the desired pharmaceutical efficacy.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R (1990) *Science* 249:1527-33, which is incorporated herein by reference.

For use in therapy, an effective amount of the TIM-3-binding molecule or TIM-3 ligand-binding molecule can be administered to a subject by any mode that delivers the TIM-3-binding molecule or TIM-3 ligand-binding molecule either systemically or to the desired surface, e.g., skin or mucosa. "Administering" the pharmaceutical composition of the present invention may be accomplished by any means known to the skilled artisan. Preferred routes of administration include but are not limited to oral, parenteral, intravenous, intramuscular, intracutaneous, subcutaneous, intradermal, subdermal, transdermal, topical, intranasal, intratracheal, inhalation, ocular, vaginal, and rectal. In certain preferred embodiments the preferred route of administration is systemic or intravenous.

The TIM-3-binding molecule or TIM-3 ligand-binding molecule, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The TIM-3-binding molecule or TIM-3 ligand-binding molecule may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the TIM-3-binding molecule or TIM-3 ligand-binding molecule in water-soluble form. Additionally, suspensions of the TIM-3-binding molecule or TIM-3 ligand-binding molecule may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the TIM-3-binding molecule or TIM-3 ligand-binding molecule may be in powder form for constitution with a suitable vehicle, e.g., sterile pyrogen-free water, before use.

For oral administration, the TIM-3-binding molecule or TIM-3 ligand-binding molecule can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the crosslinked polyvinylpyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the TIM-3-binding molecule or TIM-3 ligand-binding molecule for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. Techniques for preparing aerosol delivery systems are well known to those of skill in the art. Generally, such systems should utilize components which will not significantly impair the biological properties of the therapeutic, such as the immunomodulatory capacity of the TIM-3-binding molecule or TIM-3 ligand-binding molecule (see, for example, Sciarra and Cutie, "Aerosols," in *Remington's Pharmaceutical Sciences*, 18th edition, 1990, pp 1694-1712; incorporated by reference). Those of skill in the art can readily determine the various parameters and conditions for producing aerosols without resort to undue experimentation.

In some embodiments, topical administration is preferred. For topical administration to the skin, the TIM-3-binding molecule or TIM-3 ligand-binding molecule according to the invention may be formulated as ointments, gels, creams, lotions, or as a transdermal patch for iontophoresis. One method for accomplishing topical administration includes transdermal administration, such as by iontophoresis. Iontophoretic transmission can be accomplished by using commercially available patches which deliver a compound continuously through unbroken skin for periods of hours to days to weeks, depending on the particular patch. This method allows for the controlled delivery of the TIM-3-binding molecule or TIM-3 ligand-binding molecule and/or additional medicament through the skin in relatively high concentrations. One example of an iontophoretic patch is the LECTRO PATCH™ sold by General Medical Company of Los Angeles, Calif. The patch provides dosages of different concentrations which can be continuously or periodically administered across the skin using electronic stimulation of reservoirs containing the TIM-3-binding molecule or TIM-3 ligand-binding molecule and/or additional medicament.

For topical administration to the skin, ointments, gels creams, and lotions can be formulated with an aqueous or oily base alone or together with suitable thickening and/or gelling agents. Lotions can be formulated with an aqueous or oily base and, typically, further include one or more emulsifying agents, stabilizing agents, dispersing agents, suspending agents, thickening agents, or coloring agents. (See, e.g., U.S. Pat. No. 5,563,153, entitled "Sterile Topical Anesthetic Gel", issued to Mueller, D., et al., for a description of a pharmaceutically acceptable gel-based topical carrier.) The ointments, gels, creams, or lotions can optionally be formulated to include sunscreen compounds, fragrance, moisturizing agents, or coloring agents. Sunscreen compounds include those organic and inorganic materials employed to block ultraviolet light. Illustrative organic sunscreen compounds are derivatives of p-aminobenzoic acid (PABA), cinnamate, salicylate, benzophenones, anthranilates, dibenzoylmethanes, and camphores; examples or inorganic sunscreen compounds include zinc oxide and titanium dioxide. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks Parsol MCX and Benzophenone-3, respectively. Other examples include 2-phenylbenzimidazole-5-sulfonic acid (commercially available as Eusolex 232 from Rona), and octyldimethyl p-amino benzoic acid (octyl dimethyl PABA commercially available from Haarmann & Reimer). The exact amount of sunscreen employed in the emulsions can vary depending upon the degree of protection desired from the sun's UV radiation.

The TIM-3-binding molecule or TIM-3 ligand-binding molecule may also be formulated in rectal or vaginal compositions such as suppositories or retention enemas, e.g., containing conventional suppository bases such as cocoa butter or other glycerides.

In addition to the formulations described previously, the TIM-3-binding molecule or TIM-3 ligand-binding molecule may also be formulated as a depot preparation. Such long-acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also can include suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The TIM-3-binding molecule or TIM-3 ligand-binding molecule and additional medicament may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: acetic, benzene sulphonic, citric, formic, hydrobromic, hydrochloric, maleic, malonic, methane sulphonic, naphthalene-2-sulphonic, nitric, p-toluene sulphonic, phosphoric, salicylic, succinic, sulfuric, and tartaric. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions may be conveniently presented in unit dosage form and may be prepared by any of the methods well known in the art of pharmacy. All methods include the step of bringing the TIM-3-binding molecule or TIM-3 ligand-binding molecule into association with a carrier which constitutes one or more accessory ingredients. In general, the compositions are prepared by uniformly and intimately bringing the TIM-3-binding molecule or TIM-3 ligand-binding molecule into association with a liquid carrier, a finely divided solid carrier, or both, and then, if necessary, shaping the product.

Other delivery systems can include time-release, delayed release or sustained release delivery systems. Such systems can avoid repeated administrations of the TIM-3-binding molecule or TIM-3 ligand-binding molecule of the invention, increasing convenience to the subject and the physician. Many types of release delivery systems are available and known to those of ordinary skill in the art. They include polymer based systems such as polylactic and polyglycolic acid, polyanhydrides and polycaprolactone; wax coatings, compressed tablets using conventional binders and excipients, and the like. Bioadhesive polymer systems to enhance delivery of a material to the intestinal epithelium are known and described in published PCT application WO 93/21906. Capsules for delivering agents to the intestinal epithelium also are described in published PCT application WO 93/19660.

The compositions may, if desired, be presented in a pack or dispenser device which may contain one or more unit dosage forms containing the active ingredient. The pack may for example include metal or plastic foil, such as a blister pack. The pack or dispenser device may be accompanied by instructions for administration.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1. Generation of Th1-Specific mAb

To identify new Th1-specific cell surface proteins, Lewis and Lou/M rats were immunized with Th1 T cell clones and lines, including the established Th1-specific clone AE7 and in vitro differentiated Th1 cell lines derived from 5B6 (Waldner H et al. (2000) *Proc Natl Acad Sci USA* 97:3412-17) and DO11.10 TCR transgenic mice. Lewis and Lou/M female rats (Harlan Sprague-Dawley, Inc.) were immunized three times by a combination of subcutaneous (s.c.) injection with either $1-5 \times 10^7$ Th1-polarized T cell clones and/or lines. The rats were boosted and four days later spleen cells were fused with myeloma cells (ATCC No. CRL8006) using polyethylene glycol 1450 and selection in HAT medium. Kohler G et al. (1975) *Nature* 256:495-97. A panel of approximately 20,000 monoclonal antibodies (mAb) was generated. The supernatants from the fusion plate wells were screened by flow cytometry on Th1 and Th2 T cells. All hybridoma wells that gave a positive shift on Th1, but not Th2, T cell clones were expanded and subcloned twice by limiting dilution. Two of the mAbs that selectively stained Th1 cells, 8B.2C12 and 25F.1D6, were further characterized. These mAbs recognize a cell surface protein present on established CD4+ Th1 cells and CD8+ Tc1 cells, but absent on CD4+ Th2 cells and CD8+ Tc2 cells (FIG. 1A).

Example 2. Cloning of TIM-3

A eukaryotic expression library was constructed using mRNA from the AE7 Th1 clone and the pAXF vector. Library screening was carried out by expression cloning according to the method developed by Seed. Seed B et al. (1987) *Proc Natl Acad Sci USA* 84:3365-69. Immunoselected individual plasmids were transfected into COS cells followed by indirect immunofluorescence staining with anti-TIM-3 antibody. Positive clones were sequenced. By this method, a murine cDNA was identified that encodes a type I membrane protein of 281 amino acids with the following regions: an extracellular domain consisting of an IgV-like domain followed by a mucin-like domain consisting of 31% serine and threonine residues; a transmembrane region; and a cytoplasmic region (FIG. 1B). This gene product expressed by the cDNA was named TIM-3, T cell Immunoglobulin and Mucin domain containing molecule. The cytoplasmic region contains six tyrosines, one of which is part of a tyrosine phosphorylation motif, RSEENIY (SEQ ID NO:7). The extracellular domain contains four sites for N-linked glycosylation and five sites for O-linked glycosylation.

The human homologue of TIM-3 was identified through genomic database searches and reverse transcriptase-polymerase chain reaction (RT-PCR). It has 63% amino acid identity to murine TIM-3 overall with 77% identity in the cytoplasmic domain, including conservation of the tyrosine phosphorylation site (FIG. 1B). Database searches revealed that TIM-3 is related to Kidney Injury Molecule-1 (KIM-1)/HAVcr-1, the receptor for human hepatitis A virus, and TIM-2. All three family members (KIM-1, TIM-2 and TIM-3) have a similar Ig/mucin structure, and their genes are located on human chromosome 5q33.2 and mouse chromosome 11. McIntire J J et al. (2001) *Nat Immunol* 2:1109-1116.

Example 3. Expression of TIM-3 In Vitro

Figure 1C:
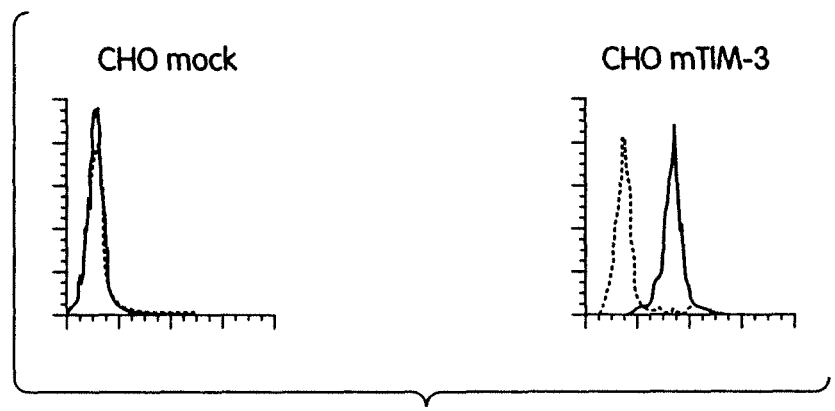
FIG. 1C is a pair of graphs depicting flow cytometric analyses of Chinese hamster ovary (CHO) cells transfected with either mTIM-3 cDNA (CHO mTIM-3) or vector alone (CHO mock). Stable puromycin-resistant cells were stained with mAb to TIM-3 (solid line) or isotype control (dotted line).

A TIM-3 cDNA expression construct was used to stably transfect Chinese Hamster Ovary (CHO) cells. Flow cytometry and immunoprecipitation analysis of the stable transfectants confirmed that the cloned protein is TIM-3 and that it is expressed at the cell surface (FIG. 1C).

Figure 1D:
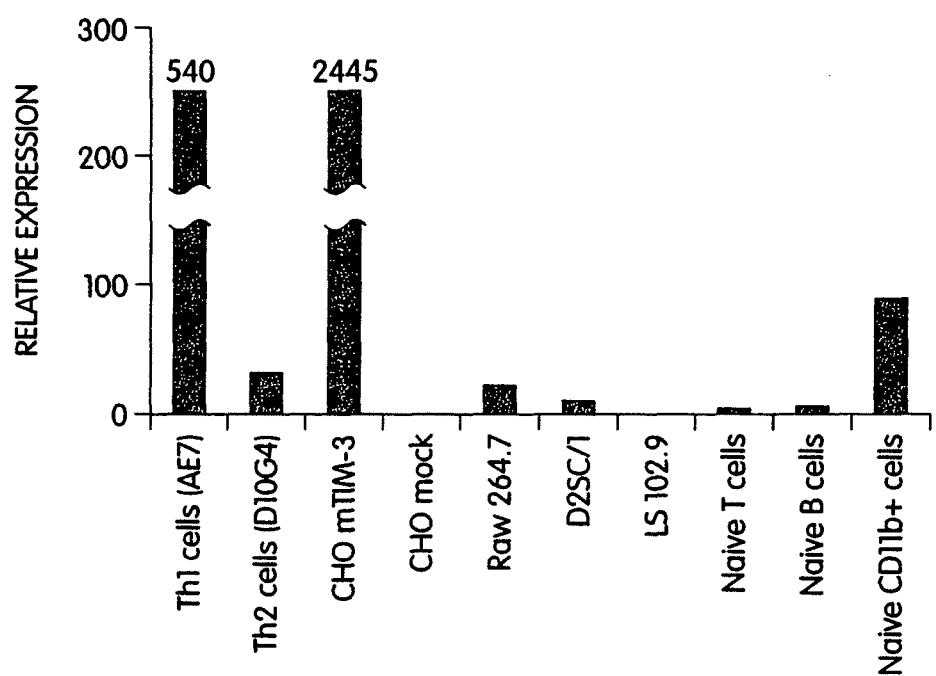
FIG. 1D is a bar graph depicting relative expression of TIM-3 RNA to control glyceraldehyde-3-phosphate dehydrogenase (GAPDH) RNA as measured by reverse transcriptase-polymerase chain reaction (RT-PCR) analysis of total RNA from various indicated cell lines and cells purified from SJL mice.

Expression of this gene in various cell lines (Th1, Th2, dendritic cell, macrophage and B cells) and SJL T, B and CD11b+ cells was determined by quantitative RT-PCR. TIM-3 transcripts were present at the highest level only in Th1 cells, although in vivo-derived CD11b+ cells also showed low-level expression (FIG. 1D). Flow cytometric analysis using anti-TIM-3 antibodies confirmed that TIM-3 is not expressed on naïve T cells, B cells, macrophages or dendritic cells. These data suggest that the molecule recognized by these antibodies is expressed mainly on differentiated Th1 or Tc1 cells and not on other hematopoietic cell types, at least at the protein level.

Example 4. Kinetics of TIM-3 Expression

Figure 2:
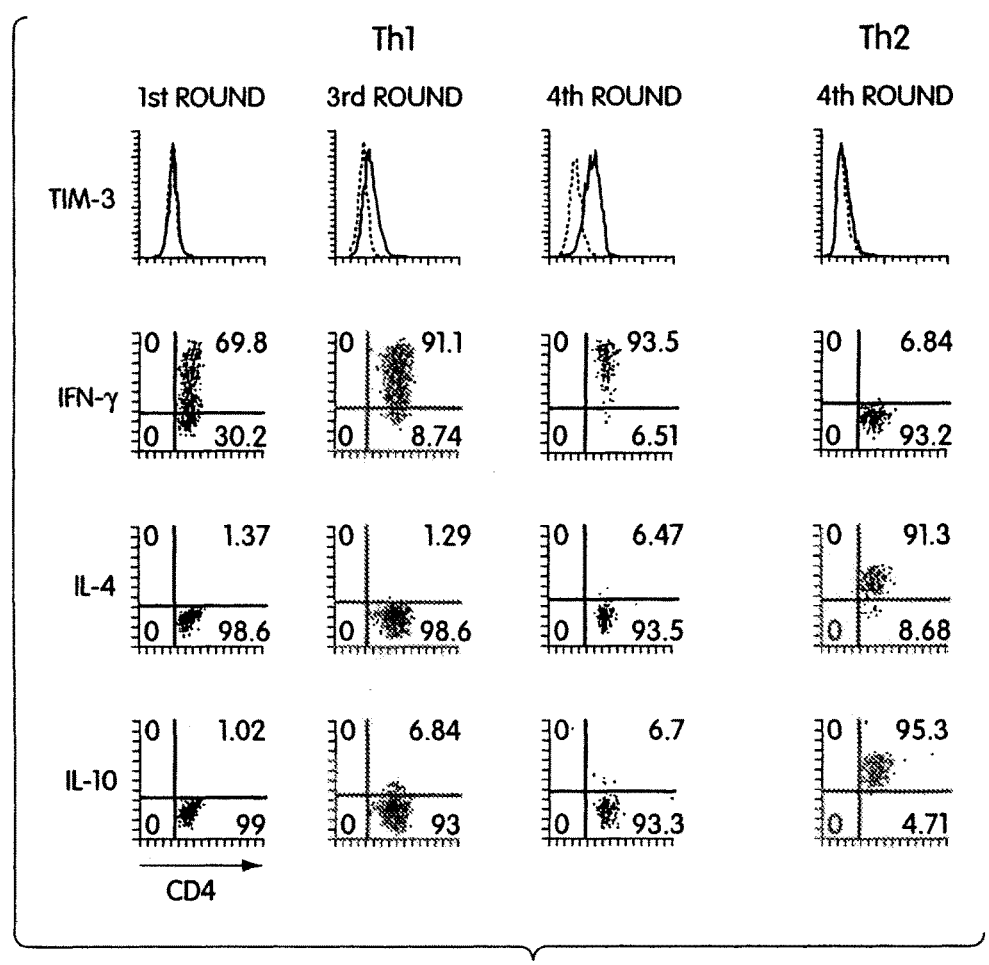
FIG. 2 is a series of graphs depicting flow cytometric analyses of TIM-3 expression on the surface of Th1 DO11.10 CD4+ T cells (solid line, specific staining; dotted line, isotype control), plus intracellular expression of IFN-γ, IL-4, and IL-10, after the various indicated numbers of rounds of stimulation under Th1- and Th2-polarizing conditions.

To examine the kinetics of TIM-3 protein expression during T cell differentiation, naïve DO11.10 TCR transgenic T cells were activated in vitro under Th1- or Th2-polarizing conditions. After each round of restimulation, Th1 and Th2 cells were stimulated with PMA/ionomycin for the induction of cytokines and then stained with mAbs to TIM-3 and CD4, and cytokine expression was detected by intracellular staining. In this experiment TIM-3 was not observed on Th2 cells but was detectable on Th1 cells after the third round of in vitro polarization (FIG. 2). TIM-3 is therefore expressed at a late stage of T-cell differentiation, suggesting that TIM-3 may not contribute to T-cell differentiation per se but can play a role in the trafficking and/or effector functions of Th1 cells.

Example 5. Expression of TIM-3 in EAE

Expression of TIM-3 was then examined during the development of EAE, a Th1-mediated autoimmune disease of the CNS. EAE-susceptible SJL mice were immunized with the encephalitogenic proteolipid protein (PLP) 139-151 peptide HSLGKWLGHPDKF (SEQ ID NO:8; Quality Controlled Biochemicals). Female SJL mice (4-8 weeks old) (The Jackson Laboratory) were injected s.c. in each flank with 50 µg of PLP 139-151 peptide emulsified in complete Freund's adjuvant (CFA; Difco) supplemented with 400 µg of *Mycobacterium tuberculosis* (Difco) for the induction of EAE. Mice were examined daily for signs of EAE, which were graded as follows: flaccid tail, 1; uneven gait and impaired righting reflex, 2; total hindlimb paralysis, 3; fore- and hindlimb paralysis, 4; and moribund, 5. Mice were scored for disease and sacrificed at various time points following immunization, and spleen, brain and lymph nodes were removed and tested for the expression of TIM-3.

Real-time reverse transcriptase-quantitative polymerase chain reaction (RT-QPCR) was performed using the Taqman® strategy (Applied Biosystems). Total RNA was isolated by TRIzol and treated with DNase I. RNA was converted to cDNA by reverse transcription, and 10 ng of cDNA was used for Taqman® PCR. The expression levels of TIM-3 and internal reference glyceraldehyde-3-phosphate dehydrogenase (GAPDH) were measured by multiplex PCR using probes labeled with 6-carboxyfluorescein (FAM) or VIC® (Applied Biosystems), respectively. TIM-3 primers and probes were designed in the 3' UTR of the 2.8 kb transcript using Primer Express v1.0 software (Applied Biosystems). The GAPDH primer/probe set was purchased from Applied Biosystems. The following TIM-3-specific primers and probe were employed for TIM-3:

```
forward primer:
                              (SEQ ID NO: 9)
CAAGCCGGTGGACCTCAGT;

reverse primer:
                              (SEQ ID NO: 10)
AGATGGGAGCCAGCACAG;

probe:
                              (SEQ ID NO: 11)
AGCTGCCTGCCCAGTGCCCTT.
```

The simultaneous measurement of TIM-3-FAM and GAPDH-VIC permitted normalization of the amount of cDNA added per sample. PCRs were performed using the Taqman® Universal PCR Master Mix and the ABI PRISM 7700 Sequence Detection System. A comparative threshold cycle ($C_T$) was used to determine gene expression relative to the no-tissue control (calibrator). Hence steady-state mRNA levels were expressed as an n-fold difference relative to the calibrator. For each sample, the TIM-3 $C_T$ value was normalized using the formula $\Delta C = C_{TTIM-3} - C_{TGAPDH}$. To determine relative expression levels, the following formula was used: $\Delta\Delta C_T = \Delta_{CT(1)sample} - \Delta_{CT(1)calibrator}$, and the value used to graph relative TIM-3 expression was calculated using the expression $2^{-\Delta\Delta C_T}$.

Figure 3A:
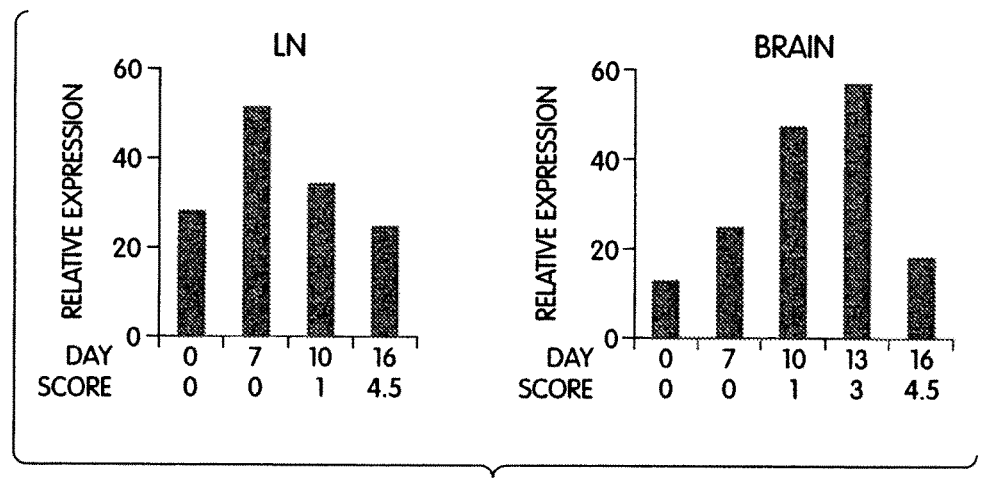
FIG. 3A is a pair of bar graphs depicting relative expression of TIM-3 RNA to control GAPDH RNA over time as measured by RT-PCR analysis of total RNA from lymph node (LN) and brain cells harvested from SJL mice at the indicated number of days following immunization with peptide PLP 139-151 for the induction of EAE. Corresponding clinical disease scores are as indicated.
Figure 3B:
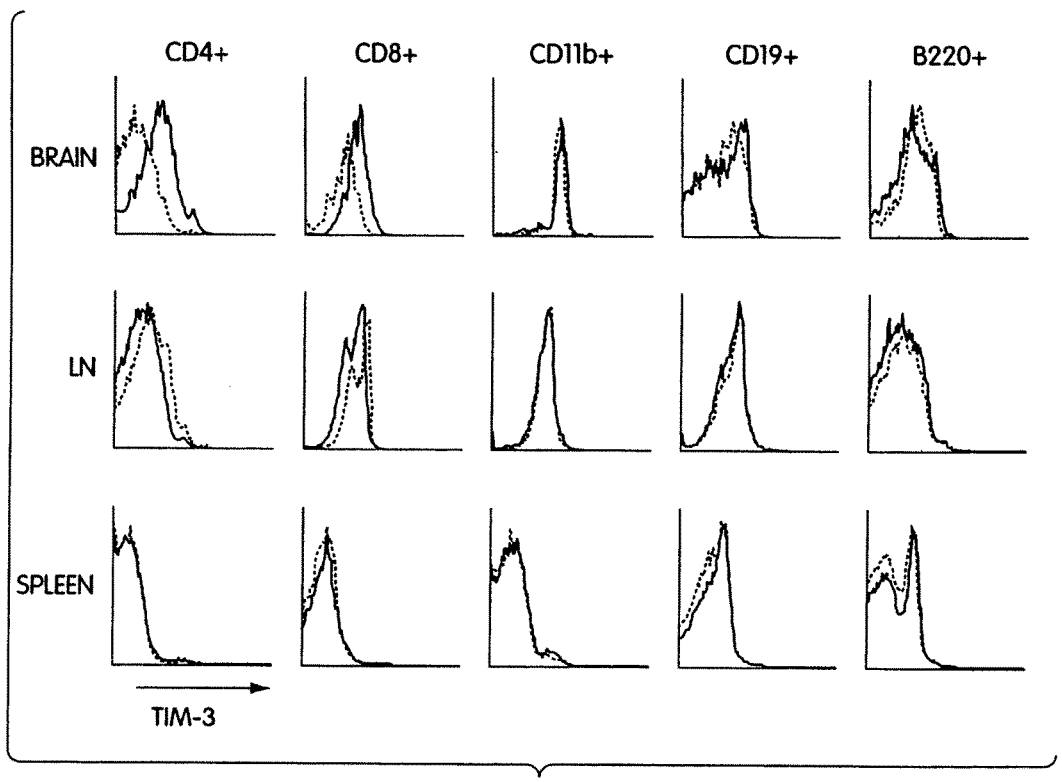
FIG. 3B is a series of graphs depicting flow cytometric analyses of TIM-3 expression on different indicated cell populations from brain, lymph node (LN), and spleen of SJL mice (solid line, specific staining; dotted line, isotype control) on day 10 following immunization with PLP 139-151 for the induction of EAE.

FIG. 3A shows expression of TIM-3 RNA relative to control GAPDH expression. Using quantitative RT-PCR, TIM-3 mRNA was demonstrated to be upregulated in the lymph node following immunization, with expression peaking at day 7 post-immunization, just prior to EAE onset. Expression in the lymph nodes was then downregulated as the disease progressed. In the brain, TIM-3 mRNA expression steadily increased and peaked at the beginning of the disease (around day 10-13). TIM-3 mRNA expression was then downregulated to near basal levels at the maximal disease score (FIG. 3A). This expression pattern was confirmed at the protein level by flow cytometric (FACS) analysis (FIG. 3B). On day 10, cells from brain, spleen and lymph nodes were stained with mAbs to TIM-3, CD4, CD8, CD11b, CD19 and B220. Histograms represent TIM-3 expression on different cell populations (dotted line, isotype control; solid line, specific staining). Whereas TIM-3 was expressed on very few CD4+ T cells (<2%) in the periphery following immunization, TIM-3 was specifically expressed on the majority of CD4+ and CD8+ T cells present in the CNS at the onset of clinical signs of disease (FIG. 3B). The number of TIM-3+ T cells decreased in the CNS as the disease progressed. These data suggest that TIM-3 is expressed in vivo on T cells and plays an important role in the initiation of EAE. These data further suggest that TIM-3 expression on differentiated Th1 cells allows Th1 cells preferentially to infiltrate CNS tissue and that TIM-3-expressing cells have an advantage for expansion in the CNS.

Example 6. Hyperacute EAE Following Administration of Anti-TIM-3

To further study the function of TIM-3 in vivo, the effect of anti-TIM-3 antibody administration on the development of EAE was tested. SJL mice previously immunized with PLP 139-151 peptide were administered anti-TIM-3 antibody or isotype-matched control rat Ig (rIgG2a) and observed for the development of EAE. Female SJL mice (4-8 weeks old) (The Jackson Laboratory) were injected s.c. in each flank with 25-75 µg of PLP 139-151 peptide in CFA supplemented with 400 µg of *M. tuberculosis*. Each mouse was also injected i.v. with 100 ng of pertussis toxin (List Biological Laboratories) in 0.1 mL of PBS. Mice were injected intraperitoneally (i.p.) every other day beginning on day 0 and continuing for 10-16 days with either 100 µg anti-TIM-3 (endotoxin activity of 0.2 to 0.8 EU/mg) or 100 µg control rIgG or PBS. Mice were examined daily for signs of EAE, which were graded as described above. At the peak of the disease or at the end of the experiment, brains and spinal cords were removed and fixed in 10% formalin and examined histopathologically for inflammation and demyelination.

Mice treated with anti-TIM-3 developed a hyperacute and atypical EAE, with increased weight loss, malaise, ataxia and paralysis of the forelimbs, without hindlimb paralysis and while sometimes retaining tail tone. While disease onset was normal in the group treated with anti-TIM-3 antibody, disease progression was accelerated and resulted in significantly more severe clinical disease and increased mortality compared to the control group treated with rIgG2a (Table 1).

Figure 4A:
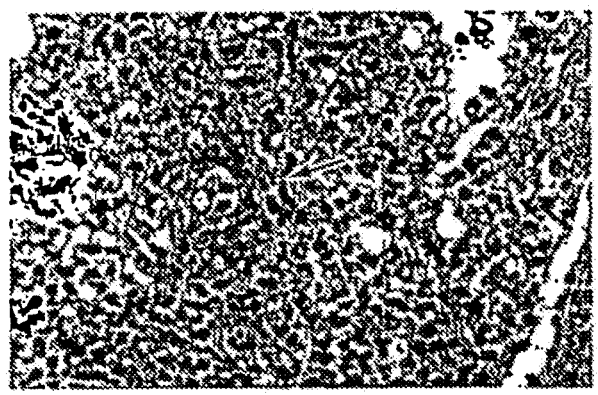
FIGS. 4A-4F are a series of photomicrographs depicting the effects of anti-TIM-3 antibody treatment on EAE.
Figure 4B:
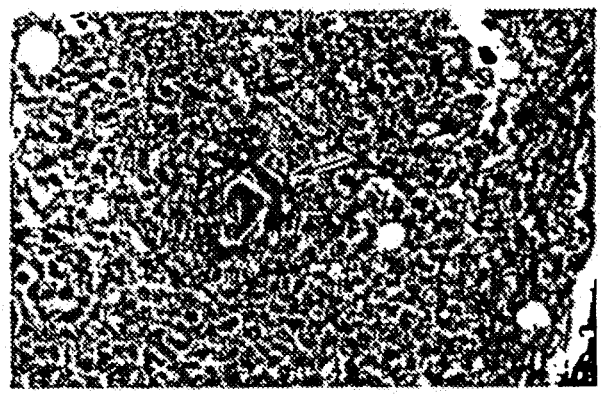
Figure 4C:
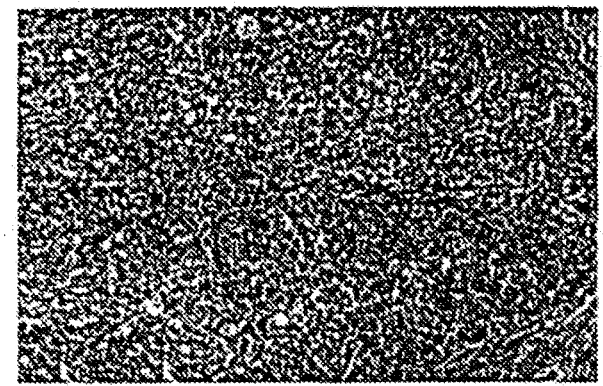
Figure 4D:
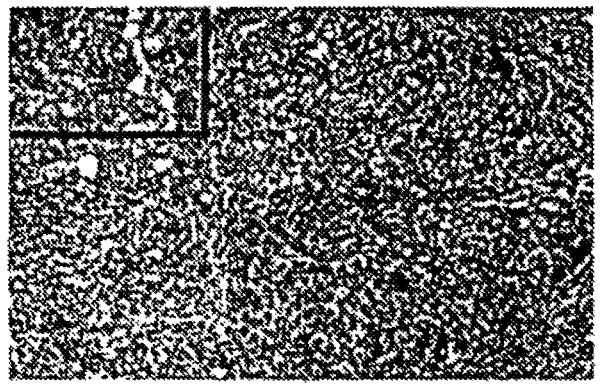
Figure 4E:
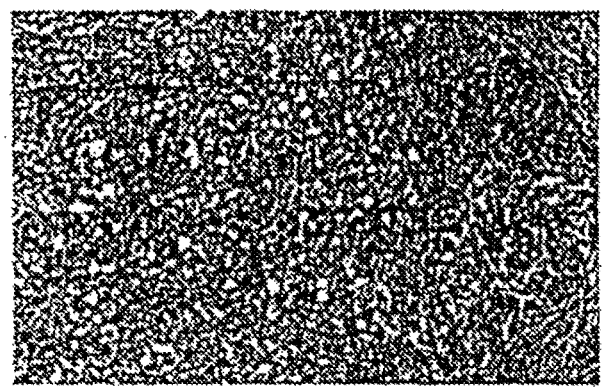
Figure 4F:
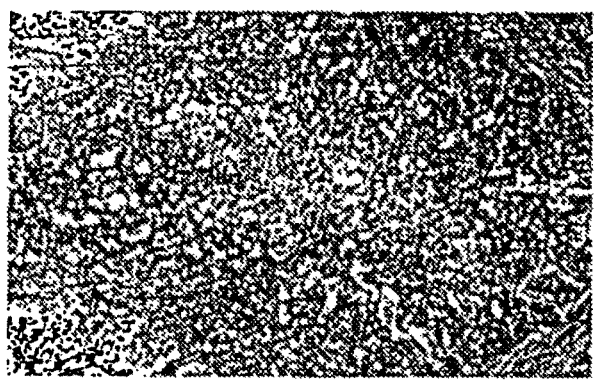

Histologically, the anti-TIM-3-treated mice generally showed typical findings of acute EAE, but with increased numbers of inflammatory foci both in the meninges and parenchyma compared to the control rIgG2a-treated group (Table 1). Anti-TIM-3-treated animals that were sacrificed immediately after the onset of clinical signs showed a preponderance of neutrophils and mononuclear cells in the CNS inflammatory infiltrates with focal perivascular fibrin deposition, indicating vascular damage and a hyperacute inflammatory response (FIG. 4A, 4B). Furthermore, anti- TIM-3-treated animals that were sacrificed at 30 days showed more extensive demyelinating lesions compared to rIgG2a-treated animals (FIG. 4C, 4D versus FIG. 4E, 4F). The demyelinating lesions in anti-TIM-3-treated mice were filled with activated macrophages with detectable phagocytosed myelin fragments (FIG. 4D, inset). It has previously been shown that activated macrophages are the primary cells responsible for demyelination in EAE (Gordon E J et al. (1995) *J Neuroimmunol* 62:153-60), and that depletion of activated macrophages leads to an inhibition of EAE. Tran E H et al. (1998) *J Immunol* 161:3767-75. Thus, it is the applicants' belief that activated macrophages induced by anti-TIM-3 antibody treatment are responsible for the hyperacute disease phenotype and enhanced inflammation and demyelination.

Figure 5A:
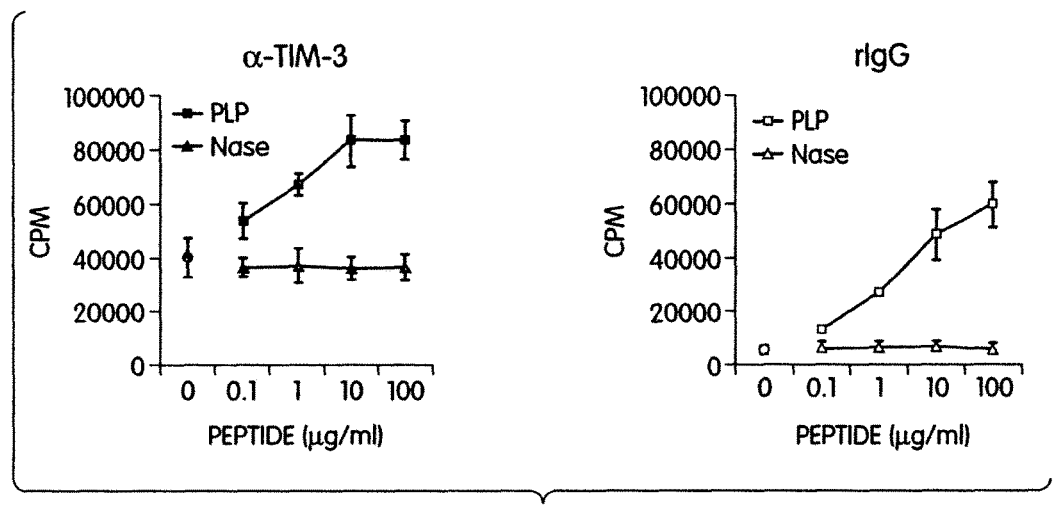
FIG. 5A is a pair of graphs depicting in vitro proliferation of splenocytes taken from SJL mice 10 days after they were immunized with PLP 139-151 and given anti-TIM-3 or control antibody (rIgG), in response to various indicated amounts of PLP 139-151 (PLP) or neuraminidase 101-120 (Nase) peptide.

Example 7. Anti-TIM-3-Mediated Activation and Proliferation of CD11b+ Cells In Vitro To further understand the function of TIM-3 in vivo and its observed role in EAE, EAE-prone female SJL mice (4-8 weeks old) were injected s.c. in each flank with 50 μg of PLP 139-151 emulsified in CFA and injected i.p. every other day with either 100 μg anti-TIM-3 or 100 μg control rIgG or PBS. Mice were sacrificed on day 10, and spleens were removed and spleen cells were isolated. The spleen cells were plated at $5 \times 10^5$ cells/well in round-bottom 96-well plates and stimulated for 48 hrs with increasing concentrations (0-100 μg/mL) of PLP 139-151 or neuraminidase 101-120 peptide EALVRQGLAKVAYVYKPNNT (SEQ ID NO:12; Nase; Quality Controlled Biochemicals) as control antigen. Plates were then pulsed with 1 μCi $^3$[H]-thymidine/ per well for 12 hrs. The incorporated radiolabeled thymidine was measured utilizing a Beta Plate scintillation counter (Wallac). Whereas spleen cells from control rIgG2a-treated mice showed a low basal (background) proliferative response (1000-5000 cpm) and a dose-dependent increase in proliferation with the addition of specific antigen, the spleen cells from anti-TIM-3-treated mice had 6-10 times the basal response in the absence of antigen, although the response to specific antigen was similar (FIG. 5A). Flow cytometric analysis of spleen cells from anti-TIM-3-treated mice revealed a 2-3 fold increase in CD11b+ cell population, i.e., the population of cells that includes predominantly monocyte/macrophages.

Figure 5B:
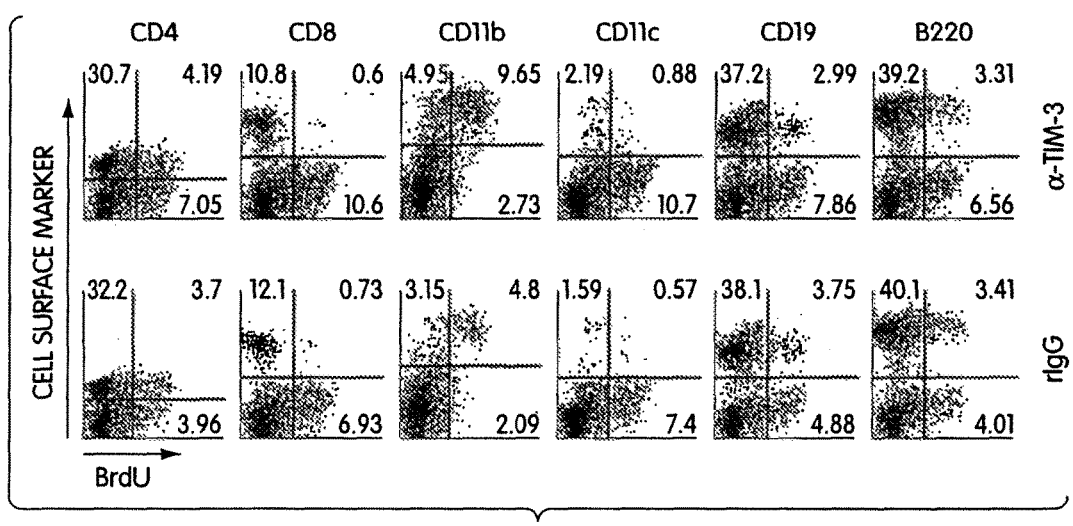
FIG. 5B is a series of graphs depicting flow cytometric analyses of various indicated populations of splenocytes taken from SJL mice 10 days after they were immunized with PLP 139-151 and given anti-TIM-3 or control antibody (rIgG).

To confirm whether CD11b+ cells in the anti-TIM-3-treated mice were proliferating and might thus contribute to the basal proliferative responses, 5-bromodeoxyuridine (BrdU) was administered in the drinking water (8 mg/mL) of immunized SJL mice treated with anti-TIM-3 or rIgG2a control antibody as above. Mice were sacrificed on day 10 and splenocytes were stained with mAbs to CD4, CD8, CD11b, CD11c, CD19, B220 and BrdU. Flow cytometric analysis of the splenocytes from anti-TIM-3-treated mice versus the splenocytes from rIgG2a-treated mice revealed an increase in the number of both BrdU+ and BrdU− cells only for CD11b+ cells (FIG. 5B). Two thirds of these CD11b+ cells incorporated BrdU and expressed higher levels of MHC class II (FIG. 5B), consistent with the view that these activated CD11b+ cells play a major role in the high basal response of anti-TIM-3 treated mice.

Figure 5C:
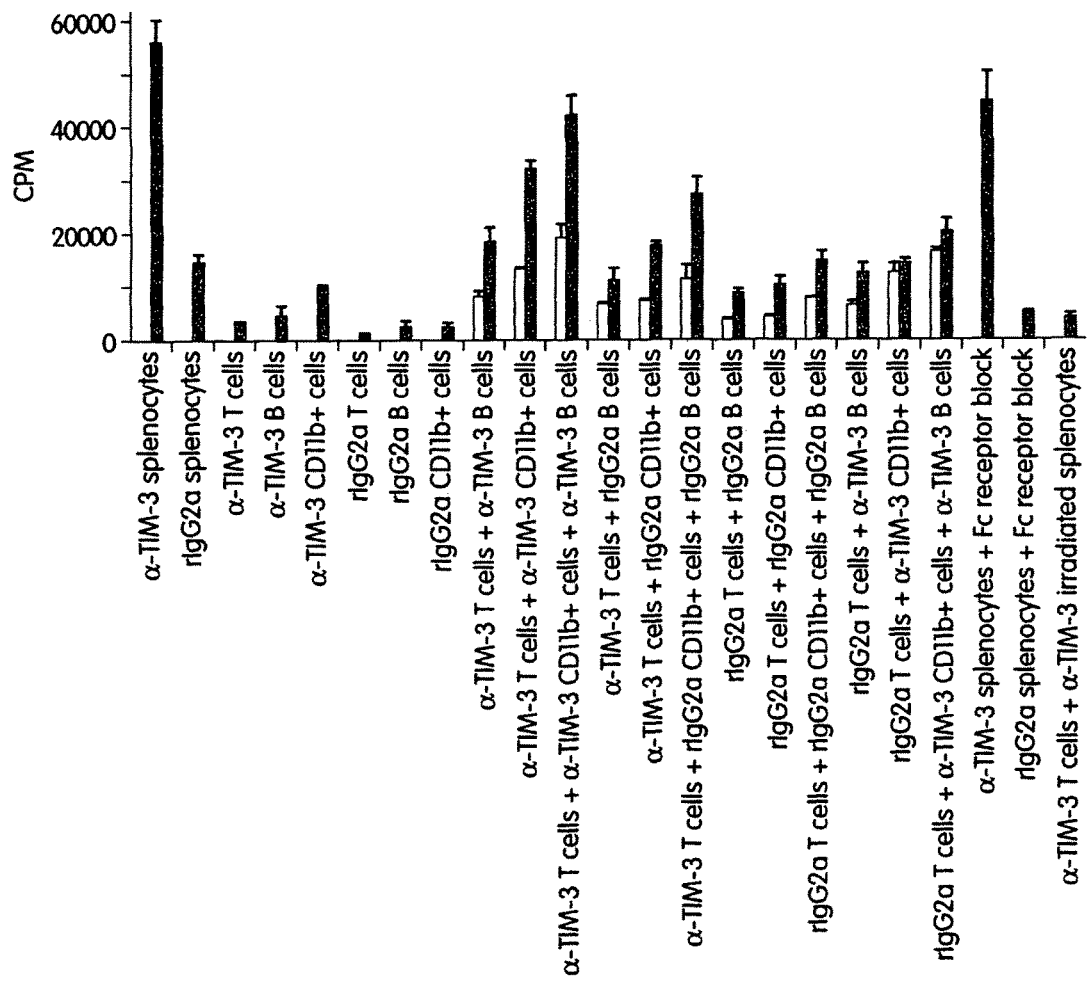
FIG. 5C is a bar graph depicting proliferative response of indicated populations of mixed and purified splenocytes taken from SJL mice 10 days after they were immunized with PLP 139-151 and given anti-TIM-3 or control antibody (rIgG2a). Gray bars, purified T cells and non-T cells separated by a permeable 0.2 μm membrane; black bars, no membrane.

Example 8. Synergistic Effect of Anti-TIM-3-Treated APC Plus T Cells on Basal Proliferative Response To determine the role of the T cells and the non-T cells, especially the CD11b+ cells, in the basal proliferative response, T cells and non-T cells were purified from the spleen cells of the anti-TIM-3- and rIgG2a-treated mice. Either whole splenocytes or T cells ($10^5$) were incubated in the presence or absence of either $2 \times 10^5$ B cells, $2 \times 10^5$ CD11b+ cells, or irradiated splenocytes, and the proliferative response was measured ($^3$H-thymidine incorporation in triplicate wells). While there was only a modest basal proliferative response from the purified T cells, B cells or CD11b+ monocytes alone from the anti-TIM-3-treated mice, the co-culturing of both B cells and CD11b+ cells with the anti-TIM-3-treated T cells recapitulated the high basal response (FIG. 5C). In comparison, the addition of either B cells, monocytes or both B cells and monocytes to the T cells from rIgG2a-treated mice produced only an additive effect (FIG. 5C (black bars)). When crisscross proliferation experiments were conducted, the addition of anti-TIM-3-treated T cells to rIgG2a-treated B cells plus CD11b+ cells increased the basal proliferative response; however, the maximal basal proliferation required the presence of both anti-TIM-3-treated non-T cells and anti-TIM-3-treated T cells. This basal proliferative response was not lowered by incubating the splenocytes with Fc receptor (FcR)-blocking antibodies, suggesting that FcR-mediated crosslinking can be excluded as the mechanism. The synergistic effect of the interaction between T cells and non-T cells was further confirmed as the addition of irradiated non-T cells to anti-TIM-3-treated T cells did not reconstitute the same high basal proliferative response.

Example 9. Cognate Interaction Between T Cells and Non-T Cells

To determine whether a cognate interaction was required between T cells and non-T cells for the increase in the basal responses, in a separate set of experiments T cells and non-T cells were separated with a permeable 0.2 μm Anapore membrane that inhibits cell contact, and proliferative responses were measured. As also shown in FIG. 5C (gray bars), separation of anti-TIM-3-treated T cells from anti-TIM-3-treated non-T cells resulted in a dramatic decrease in the proliferative responses, indicating that a cognate interaction between T cells and non-T cells is necessary.

Figure 5D:
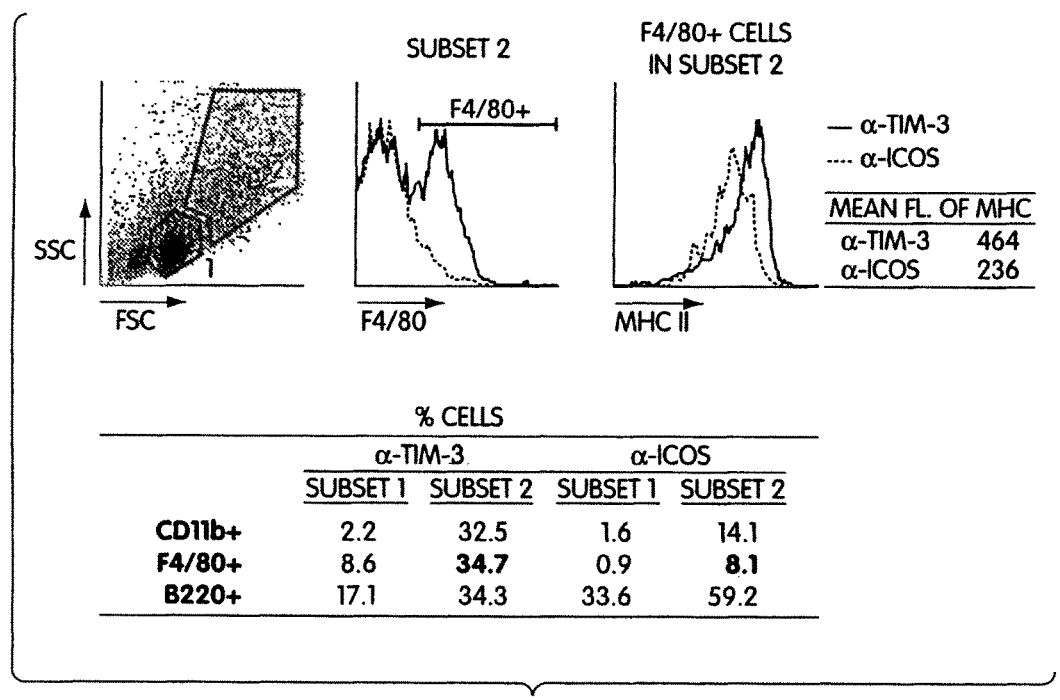
FIG. 5D is a series of graphs depicting flow cytometric analyses of spleen cells taken on day 3 from SJL mice injected on day 0 with 5×10$^6$ TIM-3-expressing, PLP 139-151 specific Th1 5B6 cells and then immunized with PLP 139-151. The recipients were also injected with anti-TIM-3 or anti-ICOS (control) antibody on days 0 and 2. FSC, forward scatter; SSC, side scatter.

Example 10. TIM-3-Expressing T Cells Regulate the Expansion and Activation of APCs To address directly whether TIM-3-expressing T cells regulate the expansion and activation of macrophages and other non-T cells, $5 \times 10^6$ TIM-3+ Th1 5B6 transgenic T cells (with specificity for PLP 139-151) were adoptively transferred to naïve SJL recipients, which were then also immunized with PLP 139-151 and treated with anti-TIM-3 or anti-ICOS antibody (as a T-cell antibody binding control) on days 0 and 2. Spleen cells were removed on day 3 and the cells were stained with mAbs to CD11b, F4/80, B220 and MHC class II. Flow cytometric analysis of the spleen cells three days after transfer showed a dramatic increase in the number of activated CD11b+/F4/80+ macrophages in the anti-TIM-3-treated group, but not in the anti-ICOS-treated mice. There was a 2-3 fold increase in the number of CD11b+/F4/80+ cells present in subset 2 (FIG. 5D). These F4/80+ macrophages also expressed higher levels of MHC class II, indicating that they were more activated.

Taken together, these data indicate that a cognate interaction between non-T cells and TIM-3-expressing Th1 cells is affected by anti-TIM-3 treatment, resulting in the expansion and activation of CD11b+/F4/80+ macrophages. Several possible mechanisms may explain this finding: a) Anti-TIM-3 may cross-link TIM-3 protein on the surface of differentiated Th1 cells in vivo and amplify the production of pro-inflammatory cytokines (e.g., IFN-γ and TNF), which in turn may induce activation of macrophages; b) anti-TIM-3 antibody could enhance migration of differentiated Th1 cells into the brain where these cells may increase the cellular influx of macrophages from the circulation; c) anti-TIM-3 could block a cognate interaction of TIM-3 with its potential inhibitory ligand on macrophages, thus leading to enhanced macrophage activation in the presence of pro-inflammatory cytokines produced by Th1 cells. It is to be understood that these different possible mechanisms of action are not necessarily mutually exclusive, nor are they to be understood to exclude any other mechanism of action.

Additionally, since Th1 cells and Th2 cells cross-regulate each other's functions, expression of TIM-3 on Th1 cells and subsequent trafficking of TIM-3-bearing Th1 cells to target tissue sites is believed also to have a role in the regulation of asthma and atopy. Thus TIM-3, in addition to being a molecule that is selectively expressed on the surface of Th1 cells, plays a functional role in macrophage activation and increased severity of an autoimmune disease. These data together with the results in asthma-resistant mice suggest that TIM-3 gene family members play an important role in the regulation of autoimmunity and allergy.

Example 11. TIM-3 Promotes Trafficking of Th1 Cells to Target Tissues

In addition to its role in macrophage activation, TIM-3 has a role in trafficking of effector Th1 cells. More specifically, TIM-3 expression promotes trafficking of Th1 cells into sites of inflammation and into the target tissues where they can mediate tissue injury and autoimmunity. Thus affecting the expression of TIM-3 on the surface of Th1 cells or interaction of TIM-3 with its ligand might either inhibit or enhance the trafficking of the Th1 cells into the tissue sites to mediate immune response and inflammation.

Figure 6A:
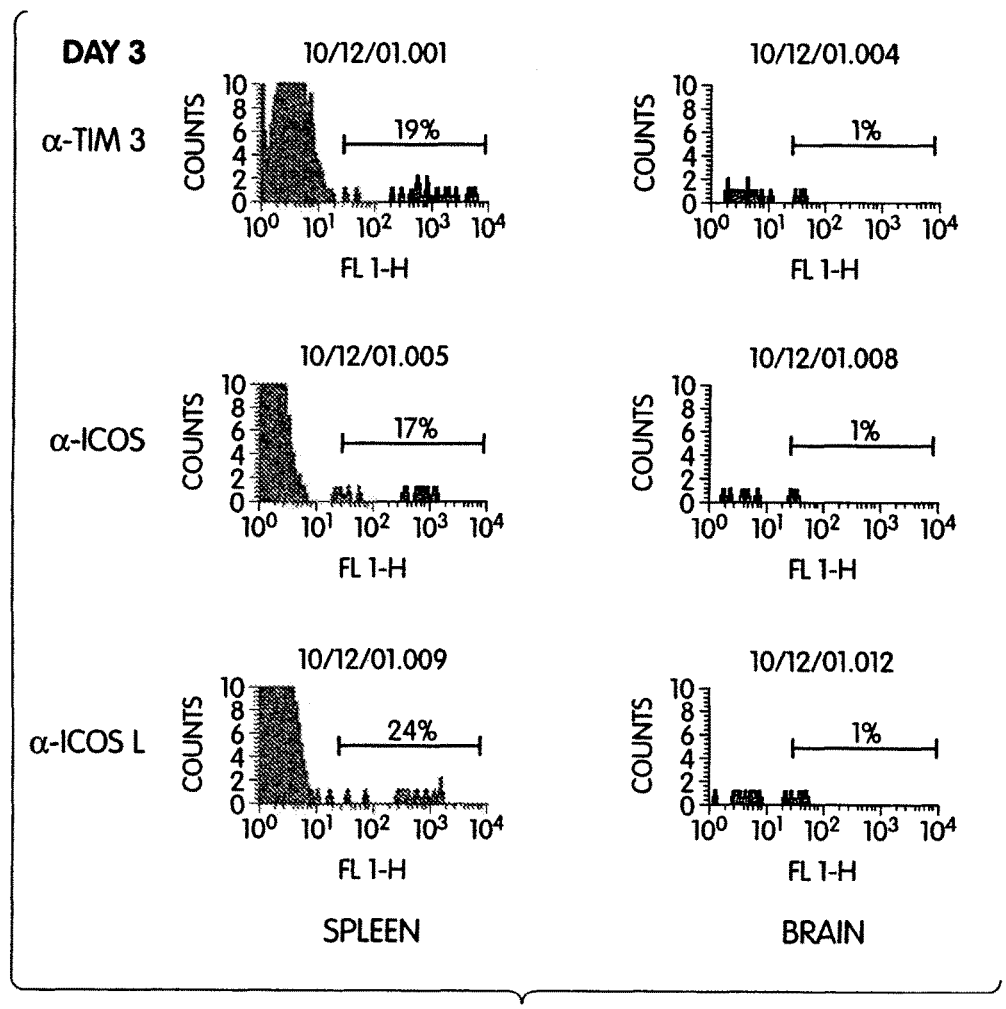
FIG. 6A is a series of graphs depicting flow cytometric analyses of CFSE-labeled T cells taken on day 3 from spleens and brains of SJL mice injected on day 0 with 1×10$^7$ TIM-3-expressing, PLP 139-151 specific Th1 5B6 cells and then immunized with PLP 139-151. The recipients were also injected with anti-TIM-3, anti-ICOS (control), or anti-ICOSL (control) antibody on days 0 and 2.
Figure 6B:
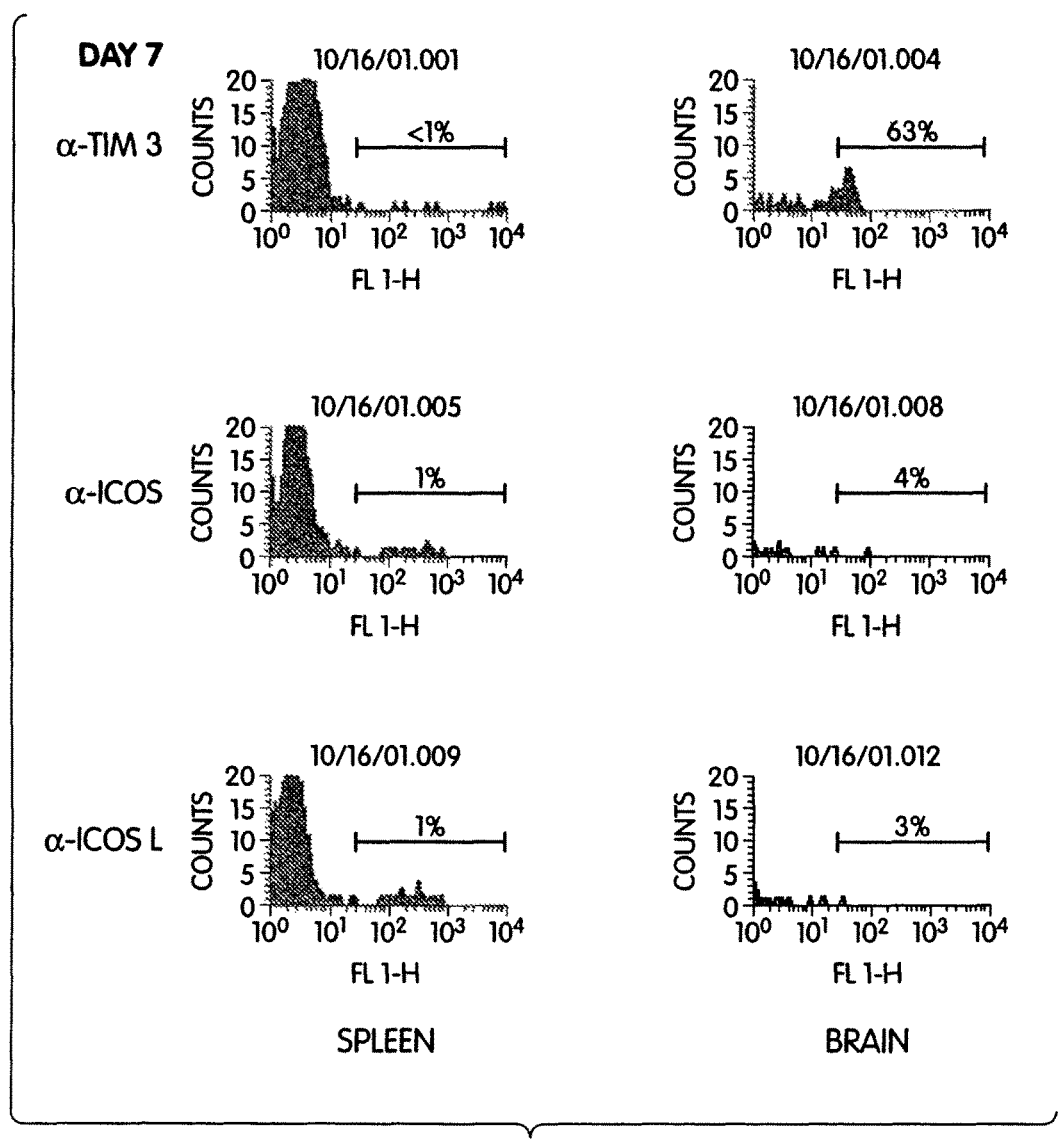
FIG. 6B is a series of graphs depicting flow cytometric analyses of CFSE-labeled T cells taken on day 7 from spleens and brains of SJL mice injected on day 0 with 1×10$^7$ TIM-3-expressing, PLP 139-151 specific Th1 5B6 cells and then immunized with PLP 139-151. The recipients were also injected with anti-TIM-3, anti-ICOS (control), or anti-ICOSL antibody on days 0, 2, 4, and 5.

The following experiment was performed to test the hypothesis that expression of TIM-3 promotes trafficking of differentiated Th1 cells to target tissue. PLP 139-151 specific transgenic T cells derived from 5B6 transgenic mice were activated and polarized under Th1 conditions. All the cells were tested for TIM-3 expression by FACS staining. The activated, polarized T cells were harvested 10 days after the final activation and stained with the dye 5,6-carboxyfluorescein diacetate succinimidyl ester (CFSE), which marks these cells and which dilutes as the cells divide. In brief, the 5B6 Th1 cells were incubated at room temperature in PBS supplemented with 3 μM CFSE (Molecular Probes, Eugene, Oreg.) at $1 \times 10^7$ cells/mL for 5-10 min. The cells were subsequently washed in RPMI, resuspended in PBS, and transferred ($1 \times 10^7$ cells/mouse) into naïve syngeneic recipients. The recipients were then immunized with the PLP 139-151 peptide in CFA and were also given 100 μg of anti-TIM-3 or control antibodies (anti-ICOS or anti-ICOSL) every other day during the course of the experiment. The mice were sacrificed on day 3 and day 7, and the presence and number (percentage) of CFSE-labeled cells were analyzed in the lymph nodes, spleens and brains of the transferred mice by flow cytometry. On day 3 post-transfer, the CFSE-labeled cells were detected only in the spleens and not in the lymph nodes or brains of the transferred recipients (FIG. 6A). However, on day 7 in the group treated with anti-TIM-3 antibody, the vast majority of CFSE-labeled cells were detected in the brains with a decrease in the number of CFSE-labeled cells in the spleen (FIG. 6B). In contrast, in the control antibody-treated groups the vast majority of the CFSE-labeled cells were still detected in the spleens of these mice and very few cells were detected in the brains of these mice (FIG. 6B). The results of this experiment suggest that anti-TIM-3 antibody treatment in vivo accelerates migration and trafficking of the TIM-3-expressing T cells into tissue sites including the CNS and thus enhances EAE induction.

Taken together, the data showing expression of TIM-3 on the majority of the infiltrating T cells in the CNS tissue and enhanced migration of the cells into the CNS following anti-TIM-3 treatment strongly support the role of TIM-3 in trafficking to the target tissue.

Example 12. TIM-3 Ligand is Expressed on APCs

Figure 7:
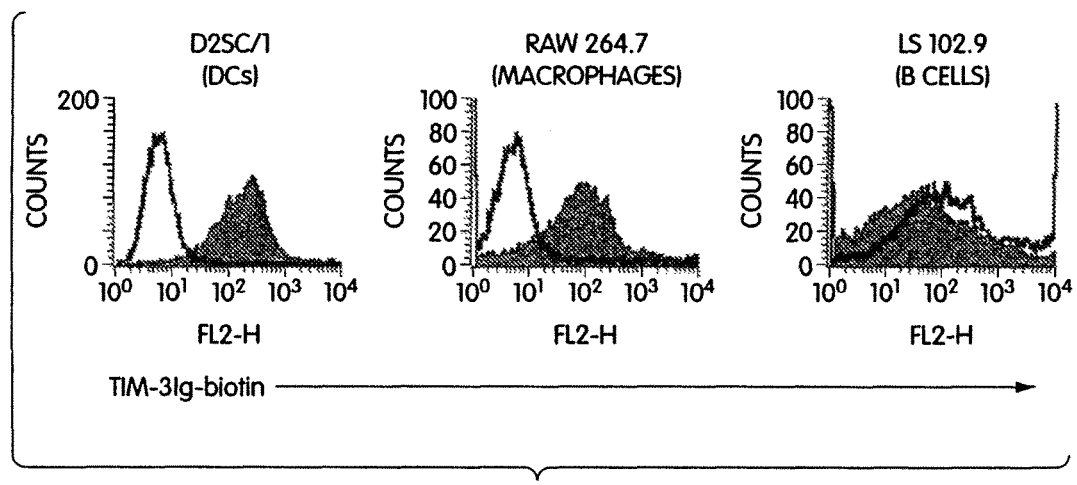
FIG. 7 is a series of graphs depicting flow cytometric analyses of various indicated cell lines (dendritic cell (DC), macrophage, and B cell) as stained by a biotinylated soluble TIM-3 protein (TIM-3Ig-biotin).

To further elucidate the mechanism for activation of macrophages and CD11b+ cells by crosslinking of TIM-3 on Th1 cells, an experiment was performed to establish the presence of a ligand or receptor for TIM-3 expressed on macrophages and other CD11b+ cell. A soluble TIM-3Ig fusion protein was prepared, in which TIM-3 was genetically fused with human immunoglobulin constant region. This soluble protein was biotinylated and used in flow cytometry experiments to identify the ligand for TIM-3 on various cell types. As shown in FIG. 7, using this reagent it was observed that soluble TIM-3Ig bound to cells of a dendritic cell (D2Sc1) cell line and macrophage (RAW 264.7) cell line, but only weakly, if at all, to cells of a mouse B cell line (LS 102.9). Additional studies demonstrated TIM-3Ig bound to normal mouse cells in vitro and to CD11b+ cells in vivo.

Example 13. Soluble TIM-3

Full-length and alternatively spliced forms of murine TIM-3 were isolated using a RT-PCR based approach. Primers were designed in the 5' and 3' untranslated region (UTR) of the murine TIM-3 gene, and subjected to PCR using cDNA generated from concanavalin A activated splenocytes. Two amplicons, of approximately 1 kb and 800 bp in size, were cloned and sequenced. The predicted amino acid translation of the 1 kb amplicon demonstrated an open reading frame consisting of a signal peptide, IgV, mucin, transmembrane, and cytoplasmic domains. In contrast, analysis of the open reading frame from the 800 bp product demonstrated the presence of only the signal peptide, IgV, and cytoplasmic domains. A deduced amino acid sequence for the alternatively spliced, soluble form of TIM-3 is provided as SEQ ID NO:13.

```
Amino acid sequence of alternatively spliced form of TIM-3
                                                        SEQ ID NO: 13
MFSGLTLNCV LLLLQLLLAR SLEDGYKVEV GKNAYLPCSY TLPTSGTLVP MCWGKGFCPW    60

SQCTNELLRT DERNVTYQKS SRYQLKGDLN KGDVSLIIKN VTLDDHGTYC CRIQFPGLMN   120
```

```
-continued
DKKLELKLDI KAGYSCKKKK LSSLSLITLA NLPPGGLANA GAVRIRSEEN IYTIEENVYE    180

VENSNEYYCY VNSQQPS                                                  197
```

Absence of the mucin domain and transmembrane region was consistent with splicing of exon 3, exon 4, and exon 5 from the murine TIM-3 gene. The data is consistent with the product encoded by the 800 bp amplicon corresponding to an alternatively spliced, soluble form of TIM-3.

Example 14. Soluble TIM-3 Fusion Protein Construction

Two fusion proteins containing extracellular portions of mouse TIM-3 fused to a human Fc tail were constructed to identify potential TIM-3 ligand(s) and to determine the functional role of TIM-3 ligand in regulating T-cell responses. One construct, mTIM-3/hFc fusion protein, contains the entire extracellular portion of mouse TIM-3 (IgV and mucin domains) fused to a human Fc tail. A second construct, mTIM-3Ig/hFc fusion protein, contains only the IgV domain of mouse TIM-3 fused to a human Fc tail. This second fusion protein was constructed as the data suggesting the alternatively spliced form of TIM-3 containing only the signal peptide, IgV, and cytoplasmic domains suggests that this secreted form of TIM-3 may have an Ig-specific ligand. These two fusion proteins, being TIM-3 ligand-binding molecules, can be used to identify and interact with TIM-3 ligand.

Example 15. Hyperacute EAE Following Administration of Soluble TIM-3

To determine the effect of these soluble TIM-3 fusion protein constructs on the development of experimental autoimmune encephalomyelitis (EAE), SJL mice were immunized with 50 µg PLP 139-151 in complete Freund's adjuvant (CFA) plus 100 ng of pertussis toxin intravenously and treated with intraperitoneal administration 100 µg of mTIM-3/hFc or 100 µg of mTIM-3Ig/hFc or 100 µg of human IgG (control) or 100 µl PBS every other day from day 0-10. Mice treated with either mTIM-3Ig/hFc or mTIM-3/hFc developed a more severe form of EAE, as demonstrated by both disease severity and mortality (see Table 2). Mice treated with mTIM-3/hFc had an average disease score of 2.69 versus an average disease score of 1.86 and 1.89 for hIgG- and PBS-treated controls, respectively. Mice treated with mTIM-3/hFc also exhibited increased mortality—31.3% versus 5.8% and 5.6% for hIgG- and PBS-treated controls, respectively. This increased severity and mortality upon treatment with mTIM-3/hFc is reminiscent of the increased EAE seen in mice treated with anti-TIM-3 antibody, suggesting that either blocking or activating the TIM-3 ligand causes the same effect as blocking or activating TIM-3 itself.

TABLE 2

EAE in Mice Treated with Soluble TIM-3 or Control

| Treatment | Incidence | Mortality | Mean Day of Onset | Mean Score |
|---|---|---|---|---|
| mTIM-3/hFc | 16/16 (100%) | 2/16 (13%) | 12.3 | 2.69 |
| hIgG | 16/17 (94%) | 1/17 (5.8%) | 13.8 | 1.86 |
| PBS | 17/18 (94%) | 1/18 (5.6%) | 12.9 | 1.89 |

Figure 8A:
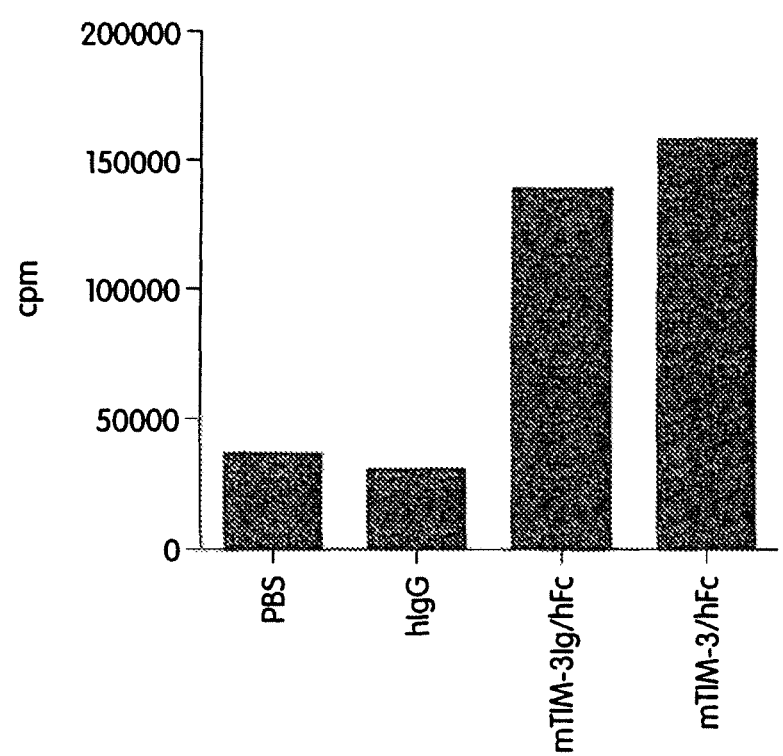
FIG. 8A is a graph depicting proliferation of splenocytes obtained from SJL mice immunized with PLP 139-151 peptide and treated for ten days with PBS, control hIgG, or soluble TIM-3 fusion protein (mTIM-3Ig/hFc or mTIM-3/hFc).
Figure 8B:
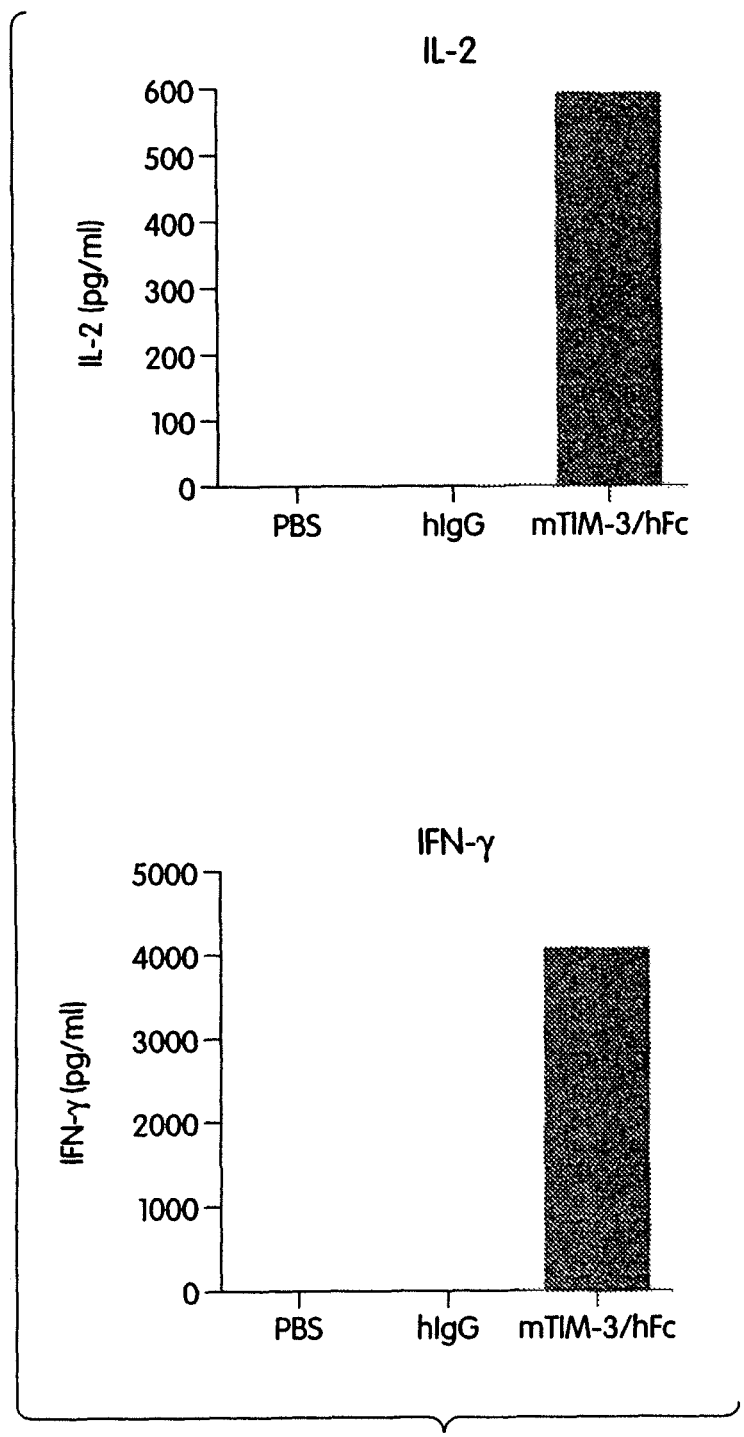
FIG. 8B is a pair of graphs depicting the stimulatory effect of mTIM-3/hFc on secretion of Th1 cytokines IL-2 and IFN-γ.

Example 16. Soluble TIM-3-Mediated Activation and Proliferation of Spleen Cells To better understand the in vivo mechanism that leads to this increased EAE, SJL mice that were immunized and treated with fusion protein or control as described in Example 15 were sacrificed on day 10, and spleens were removed. Whole spleen cells were plated at $5 \times 10^5$ cells/well for a proliferation assay measured by thymidine incorporation. While basal proliferation for hIgG- and PBS-treated controls was low (approximately 10,000 cpm), spleen cells from mice treated with mTIM-3/hFc (approximately 60,000 cpm) or mTIM-3Ig/hFc (approximately 140,000 cpm) proliferated at very high levels without peptide restimulation (FIG. 8A). This result is again reminiscent of that seen when mice were treated with anti-TIM-3 antibody. Cytokine production was measured by sandwich ELISA on supernatants taken at 48 h. Mice treated with mTIM-3/hFc produced high levels of IFN-γ (4111 pg/ml) and IL-2 (592 pg/ml), while hIgG- and PBS-treated controls did not produce any IFN-γ or IL-2 (FIG. 8B). Mice treated with mTIM-3/hFc also produced three times more IL-4 than hIgG-treated controls (FIG. 8B). Taken together, this data demonstrates that whole spleen cells taken from treated mice with either mTIM-3Ig/hFc or mTIM-3/hFc are highly activated and produce large amounts of Th1 cytokines (IFN-γ and IL-2) as well as significant amounts of Th2 cytokine IL-4. No IL-10 or TNF-α was detected.

To see what types of cells compose the activated spleen milieu of mTIM-3/hFc-treated mice, whole spleen cells taken on day 10 after immunization and fusion protein treatment were stained directly ex vivo and subjected to FACS analysis. CD4+ and CD8+ T cells from spleens of mice treated with mTIM-3/hFc expressed significantly higher levels of activation markers CD25 and CD69 than did corresponding cells from mice treated with negative control hIgG or PBS. This data indicated that T cells from spleens of immunized SJL mice treated with mTIM-3/hFc are highly activated without peptide restimulation.

Example 17. Use of Soluble TIM-3 to Identify TIM-3 Ligand

To determine what cell(s) may express the TIM-3 ligand(s), the mTIM-3/hFc and mTIM-3Ig/hFc fusion proteins were used for staining naïve spleen cells from SJL, NOD, BALB/c and C57BL/6 mice. Individual populations of spleen cells were identified by co-staining with appropriately selected cell surface markers. Flow cytometric analysis revealed that mTIM-3Ig/hFc specifically stained naïve and activated CD4+ T cells. Thus one potential ligand for the alternatively spliced, soluble form of TIM-3 appeared to be expressed on CD4+ T cells.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention. All of the references, patents, and patent publications identified or cited herein are incorporated, in their entirety, by reference.

We claim:

1. A method for treating a subject in need of an enhanced immune response, the method comprising administering an effective amount of a composition comprising a soluble TIM-3 (T cell molecule with immunoglobulin and mucin domain 3) polypeptide sufficient to promote trafficking of TH-1 cells in the subject, thereby enhancing the immune response in the subject.

2. The method of claim 1, wherein the subject has cancer.

3. The method of claim 1, wherein the subject has an infection.

4. The method of claim 1, wherein the soluble TIM-3 polypeptide is administered directly to a target tissue.

5. The method of claim 1, wherein the soluble TIM-3 polypeptide is administered systemically.

6. The method of claim 1, wherein the soluble TIM-3 polypeptide is a fusion protein.

7. The method of claim 1, wherein the soluble TIM-3 polypeptide comprises at least one domain of an extracellular region of TIM-3.

8. The method of claim 7, wherein the at least one domain is an IgV domain.

9. The method of claim 8, wherein the IgV domain comprises amino acids 22-131 of SEQ ID NO; 4 or SEQ ID NO. 6.

10. The method of claim 1, wherein the soluble TIM-3 polypeptide lacks a transmembrane domain.

11. The method of claim 1, wherein the soluble TIM-3 polypeptide lacks a mucin domain.

12. The method of claim 1, wherein the soluble TIM-3 polypeptide is linked to a second polypeptide.

13. The method of claim 1, wherein the second polypeptide comprises an immunoglobulin.

14. The method of claim 1, wherein the immunoglobulin comprises IgG.

15. The method of claim 1, wherein the soluble TIM-3 polypeptide is linked to a second polypeptide using a covalent linkage.

16. The method of claim 15, wherein the covalent linkage comprises a peptide bond.

17. The method of claim 1, wherein the soluble TIM-3 polypeptide comprises SEQ ID NO: 13.

* * * * *